United States Patent [19]

Mehta et al.

[11] Patent Number: 5,753,430
[45] Date of Patent: May 19, 1998

[54] MONOCLONAL ANTIBODIES TO HEPATITIS C VIRUS AND METHOD FOR USING SAME

[75] Inventors: Smriti U. Mehta, Libertyville, Ill.; Jill Johnson, Kenosha, Wis.; Sheela M. George; Suresh M. Desai, both of Libertyville, Ill.; Larry T. Mimms, Lake Villa, Ill.; Sushil G. Devare, Northbrook, Ill.; Joan D. Tyner, Beach Park, Ill.; Mary S. Gibadlo, Palatine, Ill.

[73] Assignee: Abbott Laboratories, Abbott Park, Ill.

[21] Appl. No.: 314,128

[22] Filed: Sep. 29, 1994

Related U.S. Application Data

[63] Continuation of Ser. No. 997,439, Dec. 28, 1992, abandoned, which is a continuation-in-part of Ser. No. 648,473, Jan. 31, 1991, abandoned, and Ser. No. 648,477, Jan. 31, 1991, abandoned, each is a continuation-in-part of Ser. No. 610,175, Nov. 7, 1990, abandoned.

[51] Int. Cl.$^6$ .............. C12Q 1/70; C12N 5/18; C07K 16/08; G01N 35/576
[52] U.S. Cl. .............. 435/5; 435/331; 435/339; 436/518; 436/548; 436/820; 530/388.3
[58] Field of Search .............. 435/5, 7.93, 7.94, 435/70.21, 240.27, 331, 339; 436/518, 548, 820; 530/388.3; 935/110

[56] References Cited

U.S. PATENT DOCUMENTS

| | | | |
|---|---|---|---|
| 4,486,530 | 12/1984 | David et al. | 435/7.91 |
| 5,106,726 | 4/1992 | Wang | 435/5 |
| 5,350,671 | 9/1994 | Houghton et al. | 435/5 |
| 5,595,868 | 1/1997 | Habets et al. | 435/5 |

FOREIGN PATENT DOCUMENTS

| | | |
|---|---|---|
| 0388232 | 9/1990 | European Pat. Off. |
| WO89/04669 | 6/1989 | WIPO |

OTHER PUBLICATIONS

P.D. Griffiths et al., Rapid Diagnosis of Cytomegalovirus Infection in Immuno–compromised Patients by Detection of Early Antigen Fluorescent Foci, *Lancet* 2:1242–1244 (1984).

*Primary Examiner*—Marian C. Knode
*Assistant Examiner*—Donna C. Wortman
*Attorney, Agent, or Firm*—Cheryl L. Becker; Priscilla E. Porembski

[57] ABSTRACT

Monoclonal antibodies which specifically bind to either Hepatitis C Virus C-100 protein, Hepatitis C Virus 33C protein and Hepatitis C Virus CORE protein, and hybridomas which produce these monoclonal antibodies. Also provided are methods for using these monoclonal antibodies and assay kits containing these antibodies.

14 Claims, 5 Drawing Sheets

MONOCLONAL ANTIBODIES TO HEPATITIS C VIRUS AND METHOD FOR USING SAME

This application is a Continuation of application Ser. No. 07/997,439 filed Dec. 28, 1992 abandoned, which is a continuation in part of U.S. patent application Ser. No. 07/648,473, abandoned, and U.S. patent application Ser. No. 07/648,477, abandoned, both of which were filed on Jan. 31, 1991, which each are continuations-in-part of U.S. patent application Ser. No. 07/610,175, filed Nov. 7, 1990, abandoned, all of which enjoy common ownership and are incorporated herein by reference.

BACKGROUND OF THE INVENTION

This invention relates generally to antibodies which specifically bind to Hepatitis C Virus (HCV), and more specifically, relates to a panel of novel hybridoma cell lines which secrete monoclonal antibodies to HCV proteins C-100, 33C and CORE, and methods for using these monoclonal antibodies.

Descriptions of Hepatitis diseases causing jaundice and icterus have been known to man since antiquity. Viral hepatitis is now known to include a group of viral agents with distinctive viral organization, protein structure and mode of replication, causing hepatitis with different degrees of severity of hepatic damage through different routes of transmission. Acute viral hepatitis is clinically diagnosed by well-defined patient symptoms including jaundice, hepatic tenderness and an elevated level of liver transaminases such as Aspartate Transaminase and Alanine Transaminase.

Serological assays currently are employed to further distinguish between Hepatitis-A and Hepatitis-B. Non-A Non-B Hepatitis (NANBH) is a term first used in 1975 that described cases of post-transfusion hepatitis not caused by either Hepatitis A Virus or Hepatitis B Virus. Feinstone et al., *New Engl. J. Med.* 292:454–457 (1975). The diagnosis of NANBH has been made primarily by means of exclusion on the basis of serological analysis for the presence of Hepatitis A and Hepatitis B. NANBH is responsible for about 90% of the cases of post-transfusion hepatitis. Hollinger et al. in N. R. Rose et al., eds., *Manual of Clinical Immunology*, American Society for Microbiology, Washington, D. C., 558–572 (1986).

Attempts to identify the NANBH virus by virtue of genomic similarity to one of the known hepatitis viruses have failed thus far, suggesting that NANBH has a distinctive genomic organization and structure. Fowler et al., *J. Med. Virol.* 12:205–213 (1983), and Weiner et al., *J. Med. Virol.* 21:239–247 (1987).

Progress in developing assays to detect antibodies specific for NANBH has been hampered by difficulties encountered in identifying antigens associated with the virus. Wands et al., U.S. Pat. No. 4,870,076; Wands et al., *Proc. Natl. Acad. Sci.* 83:6608–6612 (1986); Ohori et al., *J. Med. Virol.* 12:161–178 (1983); Bradley et al., *Proc. Natl. Acad. Sci.* 84:6277–6281 (1987); Akatsuka et al., *J. Med. Virol.* 20:43–56 (1986).

In May of 1988, a collaborative effort of Chiron Corporation with the Centers for Disease Control resulted in the identification of a putative NANB agent, Hepatitis C Virus (HCV). M. Houghton et al. cloned and expressed in *E. coli* a NANB agent obtained from the infectious plasma of a chimp. Kuo et al., *Science* 244:359–361 (1989); Choo et al., *Science* 244:362–364 (1989). CDNA sequences from HCV were identified which encode antigens that react immunologically with antibodies present in a majority of the patients clinically diagnosed with NANBH. Based on the information available and on the molecular structure of HCV, the genetic makeup of the virus consists of single stranded linear RNA (positive strand) of molecular weight approximately 9.5 kb, and possessing one continuous translational open reading frame. J. A. Cuthbert, *Amer. J. Med. Sci.* 299:346–355 (1990). It is a small enveloped virus resembling the Flaviviruses. Investigators have made attempts to identify the NANB agent by ultrastructural changes in hepatocytes in infected individuals. H., Gupta, *Liver* 8:111–115 (1988); D. W.

Bradly *J. Virol. Methods* 10:307–319 (1985). Similar ultrastructural changes in hepatocytes as well as PCR amplified HCV RNA sequences have been detected in NANBH patients as well as in chimps experimentally infected with infectious HCV plasma. T. Shimizu et al., *Proc. Natl. Acad. Sci.* 87:6441–6444 (1990).

Considerable serological evidence has been found to implicate HCV as the etiological agent for post-transfusion NANBH. H. Alter et al., *N. Eng. J. Med.* 321:1494–1500 (1989); Estaben et al., *The Lancet*: Aug. 5:294–296 (1989); C. Van Der Poel et al., *The Lancet* Aug. 5:297–298 (1989); G. Sbolli, *J. Med. Virol.* 30:230–232 (1990); M. Makris et al., *The Lancet* 335:1117–1119 (1990). Although the detection of HCV antibodies eliminates 70 to 80% of NANBH infected blood from the blood supply system, the antibodies apparently are readily detected during the chronic state of the disease, while only 60% of the samples from the acute NANBH stage are HCV antibody positive. H. Alter et al., *New Eng. J. Med.* 321:1994–1500 (1989). The prolonged interval between exposure to HCV and antibody detection, and the lack of adequate information regarding the profile of immune response to various structural and non-structural proteins raises questions regarding the infectious state of the patient in the latent and antibody negative phase during NANBH infection. Therefore, there is a need for the development of assay systems to identify acute infection and viremia which may be present. Tools are needed to distinguish between acute and persistent infection and to define the prognostic course of NANBH infection, in order to develop preventive strategies.

SUMMARY OF THE INVENTION

The present invention provides a panel of highly specific and novel monoclonal antibodies that can be employed for the detection of Hepatitis C viral proteins. The monoclonal antibodies specifically bind to either C-100, 33C or CORE antigens, and do not significantly bind to 33C and CORE, C-100 and CORE, and C-100 and 33C, respectively. The hybridomas which produce (secrete) these monoclonal antibodies are identified as follows: H81C17 (A.T.C.C. deposit No. HB 10588, producing monoclonal antibody H81C17), H35C54 (A.T.C.C. deposit No. HB 10592, producing monoclonal antibody H35C54), H28C110 (A.T.C.C. deposit No. HB 10587, producing monoclonal antibody H28C110), H4C20 (A.T.C.C. deposit No. HB 10593, producing monoclonal antibody H4C20), H11C130 (A.T.C.C. deposit No. HB 10589, producing monoclonal antibody H11C130), H1C46 (A.T.C.C. deposit No. HB 10594, producing monoclonal antibody H1C46), 13-975-157 (A.T.C.C. deposit No. HB 10608, producing monoclonal antibody 13-975-157), 14-153-234 (A.T.C.C. deposit No. 10604, producing monoclonal antibody 14-153-234), 14-1350-210 (A.T.C.C. deposit No. HB 10602, producing monoclonal antibody 14-1350-210), 6-296-534 (A.T.C.C. deposit No. HB 10607, secreting monoclonal antibody 6-296-534), and 6-914-518

(A.T.C.C. deposit No. HB 10600, secreting monoclonal antibody 6-914-518). The specificity of these monoclonal antibodies enables advantageous differentiation studies, as well as prognostic and diagnostic applications in the diagnosis and evaluation of NANBH.

In a preferred assay format, a test sample which may contain HCV antigens is contacted with a solid phase to which a polyclonal or a monoclonal anti-HCV antibody or a fragment thereof has been bound, to form a mixture. This mixture is incubated for a time and under conditions sufficient for antigen/antibody complexes to form. The so-formed complexes then are contacted with an indicator reagent comprising a monoclonal or polyclonal antibody or a fragment thereof, specific for the HCV antigen attached to a signal generating compound to form a second mixture. This second mixture is reacted for a time and under conditions sufficient to form antibody/antigen/antibody complexes. The presence of HCV antigen is determined by detecting the measurable signal generated. The amount of HCV present in the test sample, thus the amount of HCV antigen captured on the solid phase, is proportional to the amount of signal generated.

Alternatively, an indicator reagent comprising a monoclonal or polyclonal antibody, or fragment thereof, specific for HCV and a signal generating compound is added to a polyclonal or monoclonal anti-HCV antibody or fragment thereof coated on a solid phase and the test sample to form a mixture. This mixture is incubated for a time and under conditions sufficient to form antibody/antigen/antibody complexes. The presence and amount of HCV present in the test sample, and thus the amount of HCV antigen captured on the solid phase, is determined by detecting the measurable signal. The amount of HCV present in the test sample is proportional to the amount of signal generated.

In another alternate assay format, one or a combination of more than one monoclonal antibody of the invention can be employed as a competitive probe for the detection of antibodies to HCV antigen. For example, HCV CORE antigens, either alone or in combination, can be coated on a solid phase. A test sample suspected of containing antibody to HCV CORE antigen then is incubated with an indicator reagent comprising a signal generating compound and a monoclonal antibody of the invention for a time and under conditions sufficient to form antigen/antibody complexes of either the test sample and indicator reagent to the solid phase or the indicator reagent to the solid phase. The reduction in binding of the monoclonal antibody to the solid phase can be quantitatively measured. A measurable reduction in the signal compared to the signal generated from a confirmed negative NANBH test sample would indicate the presence of anti-HCV CORE antibody in the test sample.

In yet another assay format, a test sample is contacted with a solid phase to which Hepatitis C Virus proteins are attached and an indicator reagent comprising a monoclonal antibody or fragment thereof specific for Hepatitis C Virus attached to a signal generating compound, to form a mixture. The mixture is incubated for a time and under conditions sufficient for antibody/antigen complexes to form. The presence of anti-Hepatitis C virus present in the test sample is determined by detecting the measurable signal generated, and comparing the signal to the measured signal generated from a known negative sample. A measurable reduction of signal of the test sample, compared to the known negative sample's signal, is indicative of the presence of anti-HCV antibodies. Competitive assays for the detection of anti-HCV antibody using antigens free in solution also can be performed.

The presence of Hepatitis C Virus can be detected in a tissue sample by contacting the tissue sample with an indicator reagent comprising a signal generating compound attached to a monoclonal antibody selected from the group consisting of an anti-HCV C100 antibody or fragment thereof, a monoclonal anti-HCV 33C antibody or fragment thereof, and an anti-HCV CORE antibody or fragment thereof, to form a mixture. This mixture is incubated for a time and under conditions sufficient for antigen/antibody complex to form. The presence of Hepatitis C Virus present in the tissue sample is determined by detecting the signal generated.

Also provided are kits for using the monoclonal antibodies of the invention.

DETAILED DESCRIPTION OF THE INVENTION

Figure 1A:
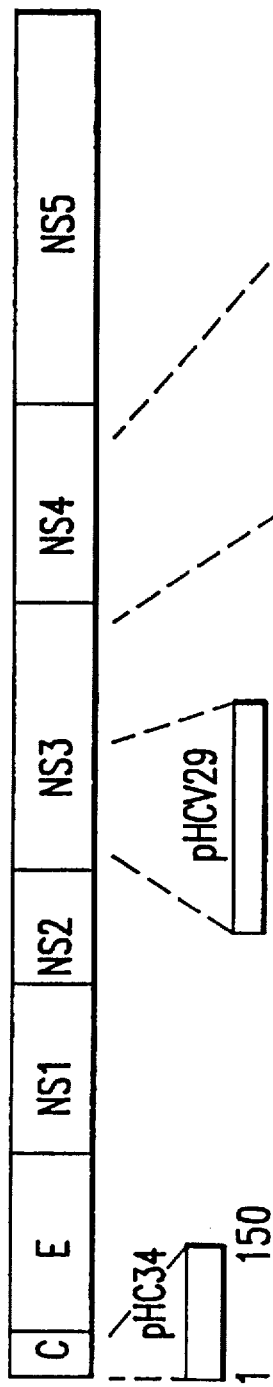
FIG. 1A is a drawing of the location of the location of the recombinant proteins on the HCV genome, employed as immunogens for generation of the hybridomas of the invention as well as that of subfragments employed for epitope mapping of the monoclonal antibodies of the invention.

The present invention provides novel monoclonal antibodies to HCV proteins C-100, 33C and CORE, methods for using the monoclonal antibodies, and kits which contain these monoclonal antibodies.

The monoclonal antibodies of the present invention can be employed in various assay systems to determine the presence, if any, of any or all of HCV proteins C-100, 33C or CORE, or a combination thereof. Fragments of the monoclonal antibodies provided also may be used. For example, in a first assay format, a polyclonal or monoclonal anti-HCV-100, anti-33C or anti-CORE antibody or a fragment thereof, or a combination thereof, which has been coated on a solid phase, is contacted with a test sample which may contain any or all of these HCV proteins or a combination of them, to form a mixture. This mixture is incubated for a time and under conditions sufficient to form antigen/antibody complexes. Then, an indicator reagent comprising a monoclonal or a polyclonal antibody or a fragment thereof, which specifically binds to either HCV C-100 protein, HCV 33C protein or CORE protein, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of HCV protein present in the test sample and captured on the solid phase, if any, is determined by detecting the measurable signal generated by the signal generating compound. The amount of HCV protein present in the test sample is proportional to the signal generated.

Alternatively, a polyclonal or monoclonal anti-HCV C-100, anti-HCV 33C or anti-HCV CORE antibody or fragment thereof, or a combination of these antibodies which is bound to a solid support, the test sample and an indicator reagent comprising a monoclonal or polyclonal antibody or fragments thereof, which specifically binds to either HCV C-100, HCV C33, or HCV CORE protein, or a combination of these antibodies to which a signal generating compound is attached, are contacted to form a mixture. This mixture is incubated for a time and under conditions sufficient to form antibody/antigen/antibody complexes. The presence, if any, of HCV protein(s) present in the test sample and captured on the solid phase is determined by detecting the measurable signal generated by the signal generating compound. The amount of HCV protein(s) present in the test sample is proportional to the signal generated.

In another alternate assay format, one or a combination of more than one monoclonal antibody of the invention can be employed as a competitive probe for the detection of antibodies to HCV protein C-100, 33C or CORE. For example, HCV proteins, either alone or in combination, can be coated on a solid phase. A test sample suspected of containing antibody to Hepatitis C Virus then is incubated with an indicator reagent comprising a signal generating compound and a monoclonal antibody of the invention for a time and under conditions sufficient to form antigen/antibody complexes of either the test sample and indicator reagent to the solid phase or the indicator reagent to the solid phase. The reduction in binding of the monoclonal antibody to the solid phase can be quantitatively measured. A measurable reduction in the signal compared to the signal generated from a confirmed negative NANBH test sample would indicate the presence of anti-HCV antibody in the test sample.

In yet another detection method, each of the monoclonal antibodies of the present invention can be employed in the detection of HCV antigens in fixed tissue sections, as well as fixed cells by immunohistochemical analysis.

In addition, these monoclonal antibodies can be bound to matrices similar to CNBr-activated sepharose and used for the affinity purification of specific HCV proteins from cell cultures, or biological tissues such as blood and liver.

The monoclonal antibodies of the invention can also be used for the generation of chimeric antibodies for therapeutic use, or other similar applications.

The monoclonal antibodies or fragments thereof can be provided individually to detect either HCV C-100, HCV 33C or HCV CORE protein. Combinations of the monoclonal antibodies (and fragments thereof) provided herein also may be used together as components in a mixture or "cocktail" of anti-HCV protein antibodies, each having different binding specificities. Thus, this cocktail can include the monoclonal antibodies of the invention directed to different antigenic determinants of the HCV genome, along with monoclonal antibodies directed to putative HCV ENV region.

The polyclonal antibody or fragment thereof which can be used in the assay formats should specifically bind to either HCV C-100 protein, HCV 33C protein or HCV CORE protein. The polyclonal antibody used preferably is of mammalian origin; human, goat, rabbit or sheep anti-HCV polyclonal antibody can be used. Most preferably, the polyclonal antibody is rabbit polyclonal anti-HCV antibody. The polyclonal antibodies used in the assays can be used either alone or as a cocktail of polyclonal antibodies. Since the cocktails used in the assay formats are comprised of either monoclonal antibodies or polyclonal antibodies having anti-HCV specificity, they would be useful for diagnosis, evaluation and prognosis of HCV infection, as well as for studying HCV protein differentiation and specificity.

Test samples which can be tested by the methods of the present invention described herein include human and animal body fluids such as whole blood, serum, plasma, cerebrospinal fluid, urine, biological fluids such as cell culture supernatants, fixed tissue specimens and fixed cell specimens. Solid supports are known to those in the art and include the walls of wells of a reaction tray, test tubes, polystyrene beads, magnetic beads, nitrocellulose strips, membranes, microparticles such as latex particles, and others.

The indicator reagent comprises a signal generating compound (label) which is capable of generating a measurable signal detectable by external means conjugated (attached) to a specific binding member for HCV. "Specific binding member" as used herein means a member of a specific binding pair. That is, two different molecules where one of the molecules through chemical or physical means specifically binds to the second molecule. In addition to being an antibody member of a specific binding pair for HCV, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to HCV as in a sandwich assay, to the capture reagent as in a competitive assay, or to the ancillary specific binding member as in an indirect assay.

The various signal generating compounds (labels) contemplated include chromogens, catalysts such as enzymes, luminescent compounds such as fluorescein and rhodamine, chemiluminescent compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

It is contemplated that the reagent employed for the assay can be provided in the form of a kit with one or more containers such as vials or bottles, with each container containing a separate reagent such as a monoclonal antibody, or a cocktail of monoclonal antibodies, employed in the assay.

The following examples demonstrate the advantages and utility of this invention for serodiagnosis of Hepatitis C virus by describing methods for the development, characterization, epitope mapping and clinical utility of these monoclonal antibodies. The methods used for monoclonal antibody development follow procedures known in the art and detailed in Kohler and Milstein, *Nature* 256:494 (1975), and reviewed in J. G. R. Hurrel, ed., *Monoclonal Hybridoma Antibodies: Techniques and Applications*, CRC Press, Inc., Boca Raton, Fla. (1982). Another method of monoclonal antibody development which is based on the Kohler and Milstein method is that of L. T. Mimms et al., *Virology* 176:604–619 (1990), which is incorporated herein by reference These examples are meant to illustrate, but not to limit, the spirit and scope of the invention.

Examples 1–8 exemplify the production and uses of cell lines 81C17, H35C54, H28C110, H4C20, H11C130 and H1C46. Examples 9–13 exemplify the production and uses of cell lines 13-975-257, 14-153-234 and 14-1350-210. Examples 14–17 exemplify the production and uses of cell lines 6-296-534, 6-914-518 and 6-1070-110.

EXAMPLES

Example 1

Immunization of Mice

E. coli derived recombinant antigens encoded by HCV sequences, designated as pHCV23 (HCV C-100, a.a. 1677–1931), pHCV29 (HCV 33C, a.a. 1192–1457) and pHCV34 (HCV-CORE, a.a. 1–150) were employed as immunogens for the generation of murine monoclonal antibodies specific for HCV C-100, 33C and CORE, respectively. Detailed information on the synthesis, cloning and expression of these recombinant proteins is disclosed in U.S. patent application Ser. No. 07/572,822, which enjoys common ownership and is incorporated herein by reference. These proteins were prepared for immunization with appropriate adjuvants after purification with protein purification methods known to those skilled in the art. FIG. 1A shows the location of recombinant HCV proteins and their subfragments on the genome.

Immunization with pHCV23

On day one, BALB/c mice received 15 μg of purified pHCV23 in 200 μl of Freund's complete adjuvant injected intraperitonially (i.p.). A second immunization was done after 14 days with 15 μg of pHCV23 in incomplete Freund's adjuvant. Mice were bled on day 21 and the immune response to pHCV was assessed by enzyme linked immunoassay (EIA) and Western blot analysis. Fusion was performed after allowing the mice to rest for at least eight weeks.

Immunization with pHCV29

On day one, BALB/c mice received 15 μg of purified pHCV29 in 100 μl of Freund's complete adjuvant injected i.p. Subsequent immunizations were done after 14 and 28 days with 15 μg of pHCV23 in incomplete Freund's adjuvant. Mice were bled on day 21 and the immune response to pHCV23 was assessed as described above.

Immunization with pHCV34

BALB/c mice were immunized following a schedule similar to that of pHCV29 immunization described above, using RIBI adjuvant system (RIBI Immunochem. Research, Hamilton, Mo.). On day one, mice received 15 μg of purified pHCV34 with 15 μg each of Trehalose dimycolate (TDM) and M. phlei in a buffer emulsion prepared according to the manufacturer's instructions. Subsequent immunizations were performed on day 14, 28 and 42. Mice were bled on days 21 and 49 and the immune response was assessed as described hereinbelow.

Enzyme-Linked Immunoassay (EIA)

The immune response to the immunizing antigen was assessed by microtiter EIA and Western blot analysis. Wells of microtiter plates were coated with 100 μl of purified antigen in 0.1M bicarbonate buffer at pH 9.5. After washing with Phosphate Buffered Saline (PBS) which also contained 0.01% sodium dodecyl sulfate (SDS) and 0.05% Tween-20® (available from Biorad Laboratories, Richmond, Calif.), free sites were overcoated with 1% BSA in bicarbonate buffer at pH 9.5. Plates were stored at 4° C. following a final wash. Sera from native or immunized mice were serially diluted in 100 μl of dilution buffer which contained 20 mM sodium phosphate, pH 7.4, 0.15M NaCl, 20% normal goat serum, 10% fetal calf serum, 5 mM EDTA, 10 mM EGTA, 50 mM Tris, 0.2% Tween-20®, with sodium azide as a preservative (at pH 6.8). The diluted sera were reacted with the antigen for three (3) hours at 37° C. The plates were washed and 100 μl of appropriately diluted goat anti-mouse IgG (heavy (H) and light (L) chain) Horseradish Peroxidase (HRPO)-conjugated antibody (Jackson Immunochemicals, West Grove, Pa.) was added. The plates were incubated at 37° C. for two (2) hours.

After a final wash, 100 μl of o-phenylenediamine:2HCl (OPD) color reagent was added. The reaction was carried out at room temperature for 10 to 30 minutes, and then stopped by the addition of 1 ml of 1N $H_2SO_4$. The absorbance at 492/600 nm was recorded, which was found to be directly proportional to the amount of specific antibody bound to the respective antigen.

Western Blot Analysis

Approximately 300 μg of purified rHCV protein were treated with SDS and 2-mercaptoethanol at 95° C., and electrophoresed in a 12% polyacrylamide-SDS gel (Laemmli et al., *Nature* 227:680–685 (1970). Proteins were transferred overnight from the gel to nitrocellulose by electrophoresis at 100 mamp, or transferred in 1–2 hours at 1.0 amp, in a standard transfer buffer which comprised 25 mM Tris [(Hydroxymethyl) Aminomethane], 192 mM glycine, and 2.0% methanol, pH 8.3. (Towbin et al., *Proc. Natl. Acad. Sci.* 73:4350–4354 [1979]). After transferring the proteins and blocking the nitrocellulose with 5% dry milk in PBS, the nitrocellulose was cut into strips (each strip containing approximately 5 ug of recombinant protein) which then were used to determine the presence of anti-HCV antibody in test sera (or other samples). Reaction mixtures consisted of a nitrocellulose strip incubated with an appropriate amount of test sample in 2.0 ml of buffer (20 mM Tris, 1 mM EDTA, 0.2M NaCl, 0.3% Triton X-100® and 2 mg/ml bovine serum albumin (BSA), pH 7.5, 5% E. coli lysate and 3% CKS lysate overnight at 4° C. The strips were washed with buffered detergent (10 mM phosphate buffered saline (PBS) pH 7.5, containing 0.1% SDS and 0.5% Triton X-100®), followed by addition of goat anti-mouse IgG antibody conjugated to HRPO. The strips were incubated for one to two hours at room temperature, followed by washing with buffered detergent. Finally, antibody bound to the protein was visualized by addition of freshly prepared HRP color reagent (Biorad Laboratories, Richmond, Calif.) (120 mg dissolved in 40 ml ice-cold methanol, then diluted into 200 ml Tris buffered saline, pH 7.8, containing 120 μl of 30% hydrogen peroxide). This assay demonstrated the presence of antibody to the respective proteins with which the mice had been immunized.

Example 2

Cell Fusion

Upon demonstration of specific anti-HCV antibody present at reasonable titers in sera of immunized mice, the mice were allowed to rest for at least eight weeks prior to a pre-fusion boost of antigen. The pre-fusion antigen boost then was performed by intravenous (IV) tail vein injection of approximately 40 µg of respective purified recombinant HCV protein. Three days later the mice were sacrificed, and their spleens which contained anti-HCV antibody-producing cells were disrupted into single cells. These single cell suspensions were treated with 0.83% $NH_4Cl$ to remove red blood cells, and then these suspensions were mixed with SP2/0 cells at a 10:1 (SP2/0:spleen cells) ratio. The mixed cells were centrifuged, washed once with serum-free medium, and again centrifuged. The fusogen polyethylene glycol (PEG) was used to form hybrids of the immune donor spleen cells with the myeloma cell line SP2/0 (HPRT neg.) Kohler and Milstein, *Nature* 256:494 (1975), and reviewed in J. G. R. Hurrel, ed., *Monoclonal Hybridoma Antibodies: Techniques and Applications*, CRC Press, Inc., Boca Raton, Fla. (1982). Briefly, fusion of the spleen and SP2/0 cells was accomplished by exposing the pellet to 40% PEG (ATTC, MW 1300–1600) in serum-free Iscoe's Modified Dulbecco's Medium (IMDM) for two minutes. The PEG and cell suspension was diluted slowly by the addition of 20 ml of serum-free IMDM over a period of five minutes, followed by collection of the cells by centrifugation. The supernatant was decanted and replaced with 30 ml IMDI containing 20% fetal bovine serum (FBS) (Hyclone Laboratories, Logan, Utah) with HAT (hypoxanthine, aminopterin and thymidine) media in order to select for hybridomas. Spleen cells from one non-immune BALB/c mouse also were added as a feeder layer. The cells were plated at 0.1 ml/well in three 96-well tissue culture plates. An additional 0.1 ml of HAT media was added to each well three days later. At weekly intervals thereafter, one-half the media was replaced with IMDM containing 20% FBS with HT (hypoxanthine and thymidine), and hybrids were allowed to grow for an additional seven to fourteen days.

It was found that some of the hybrids were composed of spleen cells making antibody to HCV fused with SP2/0 cells. Briefly, the fusogen promoted fusion of spleen cell and SP2/0 cell membranes, which formed a heterokaryon containing nuclei of both cells. Eventually, the dissimilar nuclei fuse produced a single nucleus capable of synchronous mitosis. As the fused cells divided, the hybrid stabilized by losing chromosomes of each nucleus. The fused cells were plated into multiple 96-well plates at $10^5$ to $10^6$ cells per well. The hybrid cells formed from SP2/0:spleen cell fusions were selectively propagated by culturing in HAT medium. All unused SP2/0 or SP2/0:SP2/0 fused cells were prevented from growing by aminopterin, and unfused spleen cells or spleen:spleen fused cells died off in culture. Only SP2/0:spleen cell hybrids grew in the HAT selection medium.

Example 3

Screening and Cloning of Monoclonal Antibodies

After 10 to 14 days, culture fluids from wells containing hybridoma cell growth were screened for the presence of a monospecific antibody as follows. Each of the hybridoma culture fluids was tested on a plate coated with the immunogen as well as on a plate coated with CKS protein (fusion partner used for HCV proteins) by the EIA procedure described in Example 1. Hybridoma culture fluids reacting specifically to the immunogen, i.e., HCV protein, and not the CKS fusion partner were selected for further analysis by Western blot analysis. EIA-positive hybridoma culture fluids were tested for their reactivity to the respective HCV proteins as well as CKS by Western blot analysis as described in Example 1. Hybrid samples reacting specifically with the HCV protein but not with the CKS protein by both EIA and Western blot were identified, and selected for cloning by the limiting dilution method, using the guidelines outlined by J. W. Goding, *Monoclonal Antibodies: Principles and Practices*, Academic Press, New York (1983). Culture supernatant of cloned samples were tested again by EIA with the immunogen and the CKS protein as described above in Example 1, for the confirmation of monospecific reactivity to HCV protein sequence. Clones with strongest reactivity to the protein of choice were selected for expansion and further analysis.

Example 4

Amplification of Antibody Yields by Ascites Method

In order to obtain greater amounts of monoclonal antibodies, 10 to 20 million cloned cells of the desired hybridoma cell line were inoculated into a BALB/c mouse previously treated i.p. with 0.5 ml pristane (2,6,10,14-tetramethylpentadecane) by the method outlined in J. G. R. Hurrell, ed., *Monoclonal Hybridoma Antibodies: Techniques and Application*, CRC Press, Boca Raton, Fla. (1982). Pristane treatment enhanced growth of mouse myeloma hybrids within the peritoneum of the mouse, and the ascites fluids which formed were rich in the monoclonal antibody secreted by the hybrid cells. After formation of adequate ascites fluid (approximately seven days), the mice were sacrificed and the ascites were withdrawn from the peritoneum, clarified by centrifugation and store at $-20°$ C. Monoclonal antibodies from ascites fluid were purified using protein-A sepharose (according to J. G. R. Hurrell et al, supra). All characterization procedures described herein were performed with either culture supernatants, ascites fluids or protein-A purified IgG.

Example 5

Characterization of Monoclonal Antibodies

EIA

Enzyme-linked immunoassay as described in Example 1 was used to determine the specificity of each of the monoclonal antibodies. Briefly, clarified ascites fluids or protein-A purified IgG were reacted in serial dilutions in microtiter plates coated with either a) the immunogen (i.e., pHCV23, or pHCV39 or pHCV34), b) CKS protein (fusion partners used for cloning and expression of all three immunogens), and c) respective proteins (i.e. C-100, 33C or CORE) expressed in *E. coli* under the control of bacteriophage λpL promoter (i.e. HCV proteins expressed without CKS fusion partner). Specificity of each of the monoclonal antibodies for the respective protein was confirmed by specific activity of the monoclonal antibody to the immunogen as well as the HCV protein expressed in *E. coli* λpL but not with CKS protein. TABLE 1 illustrates the representative data for monoclonal antibodies of the invention to C-100, 33C and CORE proteins of HCV.

Western blot analysis

The general protocol for Western blot analysis is as described in Example 1, except that CKS lysate was excluded from the dilution buffer. Briefly, approximately 300 µg of either a)the immunogen (i.e. either pHCV 23, pHCV 29 or pHCV 34), or b) CKS protein (fusion partner for immunogen) or c) the respective proteins expressed in *E. coli* under the control of λpL promoter, were electrophoresed and transferred to the nitrocellulose. After blocking free sites on nitrocellulose, 2 mm side strips were cut. Each of the monoclonal antibodies was tested for reactivity against all three antigens (i.e., the immunogens, CKS and the respective HCV proteins expressed in *E. coli* λpL). Specificity of each of the monoclonal antibodies was confirmed as described for EIA analysis.

Isotype

The isotype of each of the monoclonal antibodies was determined by using an isotyping kit (Amersham, Arlington Heights, Ill.) and following the instructions included with it. Briefly, the tissue culture supernatant of each monoclonal antibody and appropriate controls were reacted at a 1:5 dilution with strips coated with specific anti-isotype antibody, provided in the kit described above. Assay protocol was followed exactly according to the manufacturer's instructions. The isotype of each monoclonal antibody of the invention is provided in TABLE 1.

Competition With Immune Human Sera

In order to establish whether each of the monoclonal antibodies recognized an epitope that is immunogenic in humans, a competition assay was performed as follows. Each of the monoclonal antibodies was tested in an assay where the monoclonal antibody competed with a human sera seropositive for antibody to C-100, 33C and CORE for the binding to the respective antigen. Briefly, a human serum from an individual infected with NANBH and strongly seropositive for antibodies to C-100, 33C and CORE proteins of HCV was included in the reaction mixture with each of the monoclonal antibodies at a final concentration of 10%. Microtiter EIA was carried out as described in Example 1. A greater than 50% inhibition in the binding of the monoclonal antibody to the respective protein by the immune human sera was considered as competitive (data presented in TABLE 1).

Example 6

Epitope Mapping

Monoclonal antibodies to HCV proteins C-100, 33C and CORE were mapped to the specific region of the protein by (a) Western blot reactivity of each of the monoclonal antibodies with subfragments of the respective HCV proteins and (b) reactivity with several synthetic peptides selected for respective protein sequences, by microtiter EIA. In addition to these two methods, monoclonal antibodies to C-100 also were mapped by PEPSCAN analysis, in order to further define the epitope recognized by these antibodies. Specific additional details for mapping will be detailed where applicable for an individual monoclonal antibody.

Reactivity of Monoclonals to Various Subfragments of Recombinant HCV proteins

Briefly, several individual oligonucleotides representing a.a. 1676–1931 of HCV genome were ligated and cloned as three separate EcoRI-BamHI subfragments into the CKS fusion vector pJO200. These three subfragments were designated as CKS-B (a.a. 1676–1790), CKS-C (a.a. 1789–1863) and CKS-D (a.a. 1861–1931) as described in FIG. 1. The detailed methods for cloning and expression of the CKS-fusion proteins are as disclosed in U.S. patent application Ser. No. 07/572,822, which enjoys common ownership and is incorporated herein by reference. Cell lysates of these clones were used as antigens on Western blot analysis for preliminary epitope mapping of anti-C-100 monoclonal antibodies. Similarly, two subfragments from HCV 22C regions designated as 33C A-CKS (a.a. 1192–1331) and 33CB-CKS (a.a. 1330–1457) also were cloned and expressed in *E. coli* as described above for FIG. 1. These lysates were used as antigens for epitope mapping of anti-33C monoclonal antibodies.

Western blot analysis of each of the monoclonal antibodies with appropriate sets of subfragments of control proteins (full length proteins as well as CKS fusion partner) was carried out as described in Example 1, except that CKS lysate was excluded from the dilution buffer. Monoclonal antibody H28C110 showed reactivity with C-100B, pHCV23 and C-100 (λpL construct) but did not react with C-100C, C-100D or CKS protein, which indicated that H28C110 specifically recognizes or binds an epitope between a.a. 1676–1790 of the HCV genome. Similarly, monoclonal antibody H4C20 recognizes (specifically binds) an epitope between a.a. 1861–1931. Based on these data, monoclonal antibody H11C130 recognizes an epitope between a.a. 1192–1331, and monoclonal antibody H1C46 recognizes (specifically binds) an epitope between a.a. 1330–1457.

Reactivity with Synthetic Peptides

Several amino acid sequences were selected from different regions of HCV proteins C-100, 33C and CORE. A list of the peptides used for the epitope mapping of these monoclonal antibodies is listed below in TABLE 2.

TABLE 2

Epitope Mapping With Synthetic Peptides

| REGION OF HCV GENOME | MONOCLONAL TESTED | PEPTIDE a.a. | REACTIVITY OF EACH WITH PEPTIDE |
|---|---|---|---|
| CORE | H81C17 | sp 1–75 | None |
|  | H35C54 | sp 35–75 | None |
| 33C | H1C46 | sp 1192–1240 |  |
|  |  | sp 1223–1240 | None |
|  | H11C130 | sp 1357–1407 |  |
|  |  | sp 1418–1457 | None |
| C-100 | H28C110 | PEPSCAN analysis (a.a. 1694–1735) | sp 1694–1750 and |
|  |  | sp 1694–1750 | sp 1684–1735; |
|  |  | sp 1684–1735 | a.a 1702–1709 |
|  |  | sp 1696–1708 | (PEPSCAN) |
|  |  | sp 1866–1930 |  |
|  | H4C20 | sp 1899–1930 | sp 1899–1930 |

Each of these peptides were assembled on a resin support by a stepwise solid phase synthesis, starting with the carboxy terminal residue. A procedure was employed similar to that described in E. Gross and T. Heinehofer, eds., Barary and Merrifield, *The Peptides* 2:1284, Academic Press, New York, N.Y. (1980), using a reaction vessel of an Applied Biosystems Synthesizer Model 430A. After cleavage of the peptide from the resin, the peptide was washed with diethyl ether and extracted in 40% acetic acid solution. Crude peptide obtained after lyophilization of the aqueous solution was employed as the antigen target for epitope mapping experiments. Briefly, each of the peptides tested was coated on microtiter wells at a concentration of 10 µg/ml in bicarbonate buffer at pH 9.5. EIA was performed in the manner described in Example 1. Monoclonal antibody showing reactivity four times the negative control was considered positive.

Figure 3:
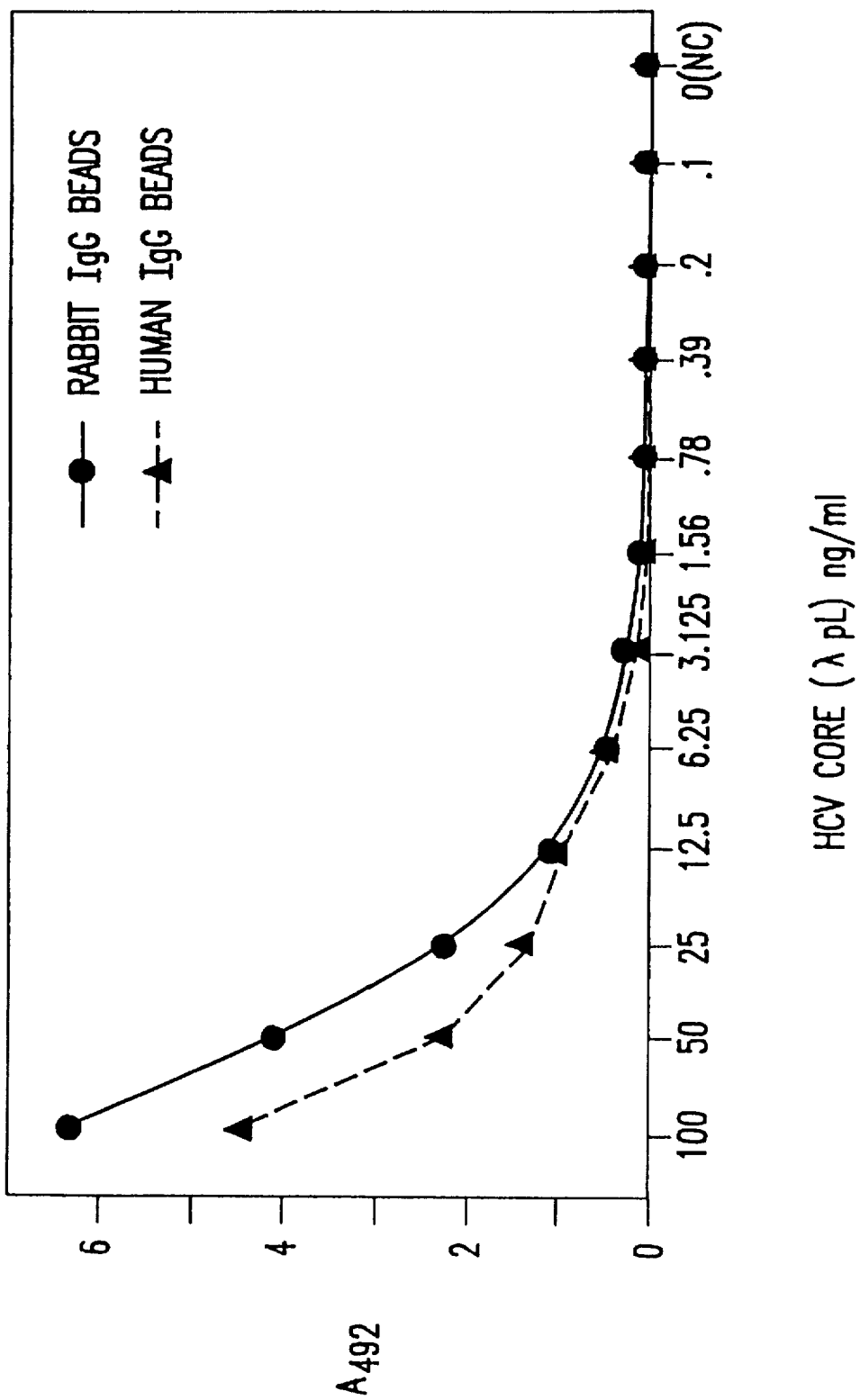
FIG. 3 is a graph illustrating the efficiency of anti-HCV rabbit and human polyclonal capture antibodies for the detection of HCV core protein in the antigen capture assay of the invention employing monoclonal antibody H81C17.
Figure 4:
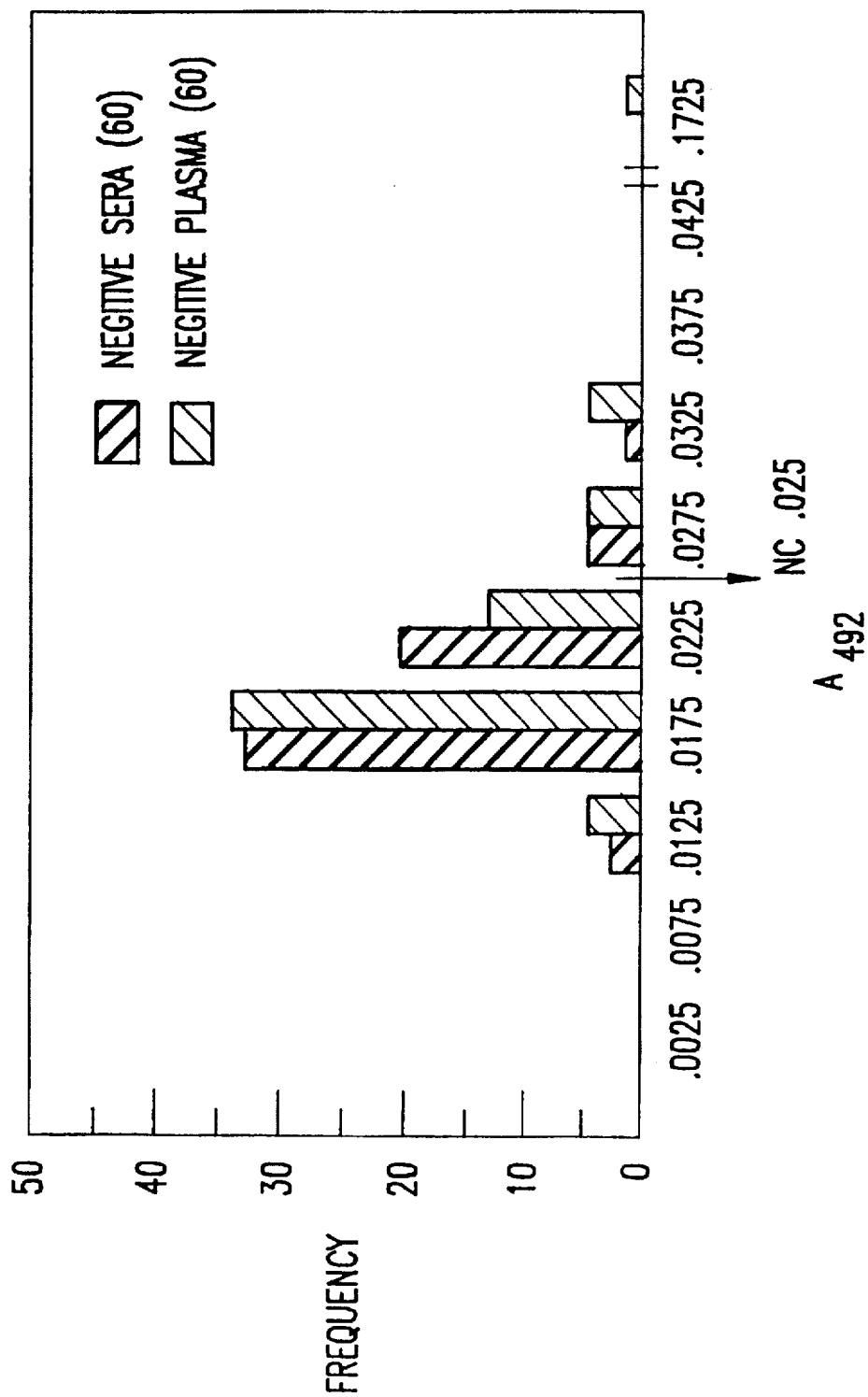
FIG. 4 is a graph of a negative sera and plasma population distribution tested by an antigen capture EIA wherein frequency is plotted against $A_{492}$.

In addition, monoclonal antibodies to HCV C-100 were also mapped with PEPSCAN analysis. Synthetic peptides were synthesized on polypropylene pins following the manufacturer's instructions (Cambridge Research Bioscience, Valley Stream, N.Y.). An EIA was performed with each of the monoclonal antibodies to HCV C-100 by the procedure outlined by the manufacturer with 67 overlapping hexamer peptides encompassing a.a. 1684–1750 of the HCV genome. Representative data are illustrated in FIG. 3. Monoclonal antibody H28C110 specifically reacted with peptide sequence a.a. 1702–1709 of the HCV genome. Monoclonal antibody H4C20 did not show reactivity in PEPSCAN but did react in EIA with a larger peptide 1899–1930 a.a. This could be due to the fact that H4C20 requires a longer peptide to recognize a linear epitope.

Example 7

EIA for the Detection of HCV Proteins in Biological Samples

For the purposes of simplification, detailed methods are described for the CORE proteins of HCV. Methods described for the preparation of rabbit polyclonal antibodies to HCV proteins 33C and C-100 were identical to that detailed hereinbelow for HCV CORE protein.

Preparation of Rabbit Polyclonal Antibodies Against HCV CORE Protein

Young rabbits (3–4 months old and weighing 2–3 kg) were obtained from Hazelton Labs, Denver, Pa. Primary immunization was carried out with 100–150 µg of highly purified HCV CORE protein (expressed in *E. coli* under λpL promoter) in Freund's complete adjuvant by intra-muscular (I.M.) injection at four different sites. Subsequently, two immunizations were carried out at two week intervals in similar fashion in Freund's incomplete adjuvant. Immune response of the rabbits was monitored by EIA and Western blot analysis as described in Example 1. Rabbits were bled when acceptable immune response to the protein was achieved. IgG from the immune rabbit sera was purified by Protein-A sepharose affinity chromatography, by methods known to those in the art.

Bead Coating

In the presently most preferred assay format, rabbit IgG prepared as hereinabove was coated on polystyrene beads as the solid support for capture of CORE antigens in the test sample. The polystyrene beads were washed with distilled water and incubated at 40° C. for two (2) hours with 5–10 µg/ml of purified HCV CORE rabbit IgG in a buffer solution (0.1M Tris, 0.5M NaCl, 0.0022% Triton X-100®, pH 8.5). The beads were washed once with PBS and then soaked in 0.1% Triton X-100® in PBS for approximately one (1) hour at 40° C. After washing twice with PBS, the beads were overcoated with 3% bovine serum albumin (BSA) in PBS for approximately one (1) hour at 40° C. Finally, the beads were overcoated with a 5% sucrose solution in PBS and dried under nitrogen. Anti-HCV human polyclonal IgG, purified from sera of individuals seropositive for HCV antibodies to C-100, 33C and CORE also was coated in similar fashion.

EIA

Several monoclonal antibodies specific for either HCV C-100, HCV 33C or HCV CORE were screened for use as the probe for detection of HCV proteins in a test sample by EIA. Briefly, each of the monoclonal antibodies was incubated with the respective antigen in the presence of polystyrene beads coated with anti-HCV rabbit polyclonal IgG. The detailed protocol for EIA was similar to that described hereinbelow. Data illustrating the reactivity of the monoclonal antibodies which showed the best reactivity as a probe for the antigen detection assay are shown in TABLE 3.

TABLE 3

| Monoclonal Antibody | Antigen | Absorbance at $A_{492}$ at Antigen Conc. | |
|---|---|---|---|
| | | NEG. CONTROL 0 ng/ml | POS. CONTROL 100 ng/ml |
| H81C17 | HCV CORE | 0.246 | >6.62 |
| H11C130 | HCV 33C | 0.194 | 0.832 |
| H28C110 | HCV C-100 | 0.623 | 2.53 |

In the EIA procedure, 200 µl of specimen which was suspected of containing antigen to HCV CORE protein was incubated in a reaction tray with 50 µl of monoclonal antibody H81C17 (at a final protein concentration of 5–10 µg/ml diluted in a buffer containing 20 mM Tris, 0.1 mM NaCl, 1 mM EDTA, 3.0% BSA, 0.3% Tween-20® and 10% FBS at pH 7.5), and a bead coated with HCV rabbit IgG (prepared as described hereinabove). After overnight incubation at ambient room temperature, the beads were washed with distilled water and 200 µl of appropriately diluted Horseradish peroxidase labeled goat anti-mouse IgG (H+L) (Jackson Immunoresearch, West Grove, Pa.) was added. Incubation with the labeled probe was carried out at about 40° C. for approximately two (2) hours. Beads were washed and transferred to reaction tubes containing 300 µl of O-phenylenediamine:2HCl (OPD) color reagent. The reaction was carried out at ambient room temperature in the dark for 30 minutes, and then it was stopped by the addition of 1 ml of 1N $H_2SO_4$. Absorbance was recorded at 492/600 nm. A negative control which was previously screened and confirmed to be negative for NANBH infection was included in the experiment. The positive control consisted of a solution of recombinant HCV CORE protein (pHCV 34) in the buffer solution described hereinabove. Triplicates of both positive and negative control were included with each set of experiments.

In order to determine the efficiency of the antigen capture assay for the detection of HCV CORE protein in a sample, various concentrations of recombinant HCV CORE protein (expressed in *E. coli* under λpL promoter), ranging from 100 ng protein/ml to 100 pg protein/ml were diluted in the buffer mentioned above. The EIA procedure was performed with each of diluted the diluted panel members following the procedure described herein. For the purpose of comparison, each of the panel members was tested with (a) anti-HCV rabbit polyclonal antibody on the solid phase and (b) anti-HCV human polyclonal antibody on the solid phase. As illustrated in FIG. 3 and TABLE 4, the antigen capture assay of the present invention detected as low as 200 pg HCV CORE protein in 200 µl of the test sample. Although there was no significant difference in the sensitivity of detection with either rabbit or human capture antibody, anti-HCV rabbit antibody showed overall superior performance in the assay and was chosen as the preferred polyclonal antibody for the antigen capture.

TABLE 4

Detection of HCV CORE Protein by Monoclonal Antibody H81C17

| CONC. OF ANTIGEN | REACTIVITY IN EIA | |
|---|---|---|
| pL CORE* ng/ml | $A_{492}$ Rabbit Bead | $A_{492}$ Human Bead |
| 100 | 6.39 | 4.45 |
| 50 | 4.06 | 2.19 |

TABLE 4-continued

Detection of HCV CORE Protein by Monoclonal Antibody H81C17

| CONC. OF ANTIGEN | REACTIVITY IN EIA | |
|---|---|---|
| pL CORE* ng/ml | $A_{492}$ Rabbit Bead | $A_{492}$ Human Bead |
| 25 | 2.19 | 1.25 |
| 12.5 | 1.02 | 0.887 |
| 6.25 | 0.339 | 0.382 |
| 3.125 | 0.230 | 0.121 |
| 1.56 | 0.084 | 0.043 |
| 0.78 | 0.050 | 0.032 |
| 0.39 | 0.038 | 0.014 |
| 0.2 | 0.028 | 0.015 |
| 0.1 | 0.020 | 0.014 |
| 0 | 0.014 | 0.014 |

*Recombinant HCV CORE expressed in *E. coli* under λpL promoter system used as the antigen. Concentrations represent ng of protein/ml based on A280 values. The assay system has 200 μl/well for testing, so the actual amount of antigen per well is one-fifth of the value given here.

Example 8

Testing of Negative Serum and Plasma Samples

Sixty sera and sixty plasma samples negative for NANBH were tested by the EIA procedure detailed in Example 7. The results of these assays are presented in FIG. 5. It can be seen by the data that the majority of negative plasma and sera fell within a tight range of O.D. (Optical Density) values close to the negative control value. One plasma sample with an O.D. of 0.1725 was found to be repeat reactive. Confirmation of the presence of antigen could not be performed on this sample due to the insufficient volume of the sample.

Example 9

Production and Use of Cell Lines 1 3-975-157. 14-153-234 and 14-1350-210

A. Production of recombinant HCV antigens and immunogens

Synthetic peptides corresponding to regions within the putative CORE domains of the HCV genome were made by automated peptide synthesizer. The following peptides were constructed utilizing methods known in the art:

CORE
1-75
35-75
35-61

These peptides are described in pending U.S. patent application Ser. No. 07/610,180, entitled HEPATITIS C ASSAY, which enjoys common ownership and is incorporated herein by reference.

Recombinant antigens were made as fusion proteins with CMP-KDO synthetase in *E. coli* according to methods known in the art, or as non fused protein with λPL promoter system. The following proteins were cloned and purified:

| λPL CORE | (1–150) | |
|---|---|---|
| CKS-CORE | (1–150) | |
| CKS-33c | (1191–1457) | |
| λPL-33c-CORE | (fusion of 1191–1457 and 1–150) | |
| CKS-BCD | (156–1930) | |
| CKS-E | (1931–2189) | (NS4/NS5 reaction) |
| CKS-B | (1676–1790) | |

Figure 1B:
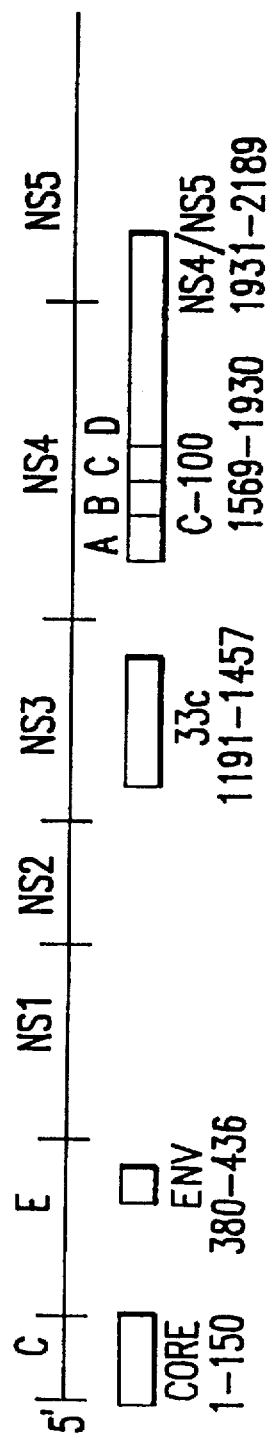
FIG. 1B is a map of the HCV GENOME representing the non-structural (NS) genes and the structural genes, core (C) and envelope (E).
Figure 2:
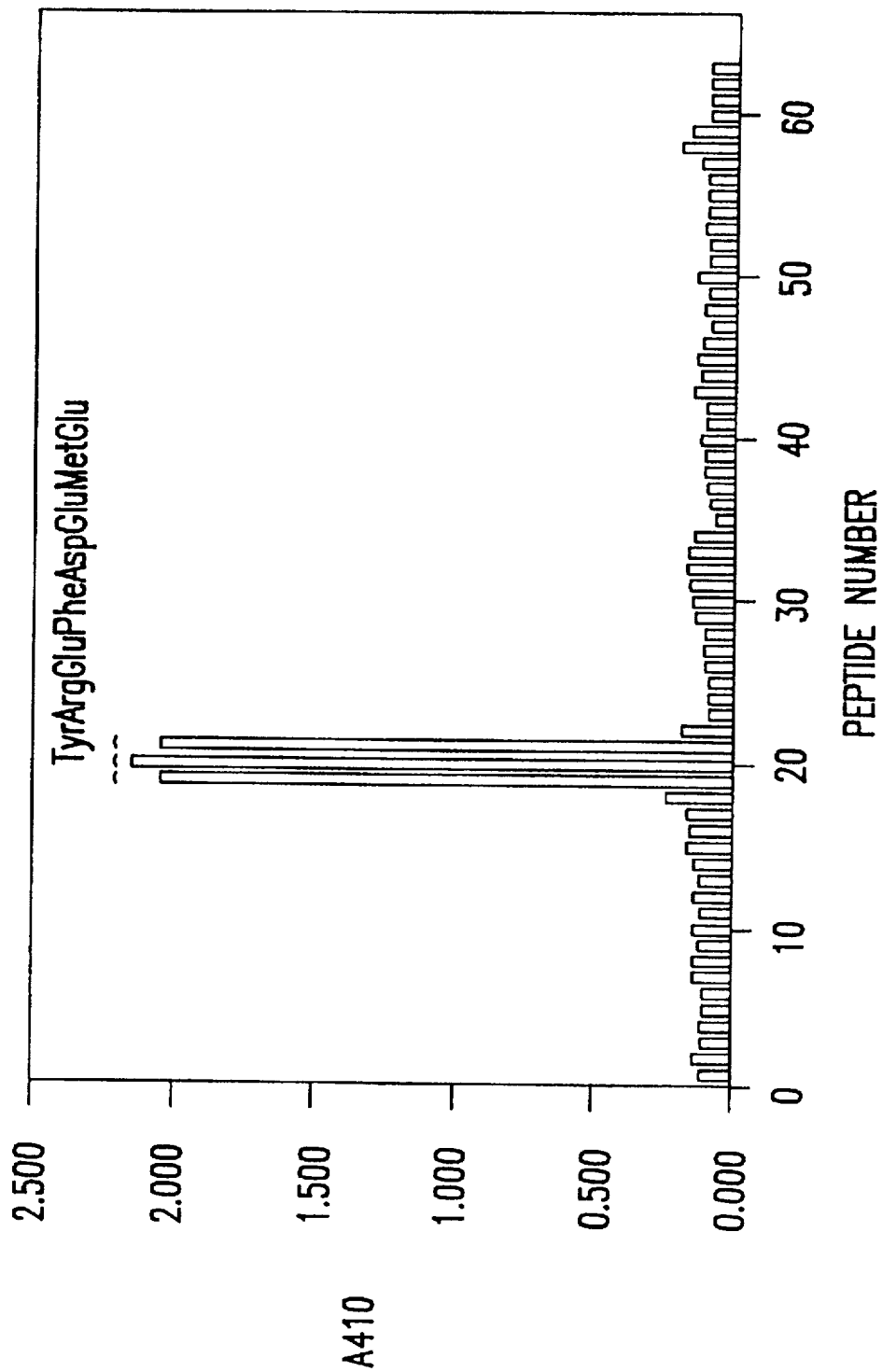
FIG. 2 is a profile of PEPSCAN analysis with overlapping hexamer peptides (a.a. 1694–1735) of monoclonal antibody H28C110 illustrating the epitope specificity and amino acid sequence of the HCV genome recognized by monoclonal antibody H28C110.

See FIG. 1B for map of HCV genome and approximate locations of HCV regions. Recombinant protein C-100 (1569–1930) was obtained from Chiron as a fusion protein with superoxide dismutase (SOD). All recombinant proteins were greater than 90% pure by SDS-PAGE.

B. Immunization of Mice

BALB/c mice (Charles River Laboratories, Charles River, N.Y.), 6–8 weeks old, were initially immunized subcutaneously and intraperitoneally with 50 μg of λPL-CORE in 100 μl of Freund's complete adjuvant (Difco, Detroit, Mich.). On day 15, 50 μg of the immunogen was diluted into 100 μl of phosphate buffered saline (PBS), pH 7.2, and injected intravenously into the tail vein (J. Goding, *Monoclonal Antibodies: Principles and Practice* [New York; Academic Press, 1986]). Sera titers were not evaluated.

C. Fusion

On day 18, mice were sacrificed and splenocytes were fused in a 1:1 ratio with the SP2/0 myeloma line according to known conventional methods (G. Kohler and C. Milstein, *Nature* (1975) 256:495–497; J. Goding, supra). The cell fusion pellet was dispersed with 1 ml 50% polyethylene glycol (PEG) (American Type Culture Collection, MW 1450) and centrifuged in Iscove's Modified Dulbecco's Medium (IMDM) (Gibco, Grand Island, N.Y.). The cells were resuspended in HAT (hypoxanthine-aminopterin-thymidine)-selective IMDM with 10% fetal bovine serum (FBS) (Hyclone Laboratories, Logan, Utah) and plated at $3 \times 10^5$ cells per 96-well tissue culture plates. Growth promoters included in the HAT media were 0.5% STM (RIBI Immunochem. Research, Inc., Hamilton, Mont.) and 1% Origen Hybridoma Cloning Factor (Igen, Rockville, Md.). Growth medium was replaced in culture wells post-fusion on day 5 and 7 using HT (hypoxanthine-thymidine) supplemented IMDM with 10% FBS.

D. Enzyme Immunoassay (EIA)

Culture supernatants were EIA screened 10 days post-fusion against the immunizing antigen to detect hybrids secreting HCV specific antibody and a non-specific protein to eliminate any false positives (Langone & Van Vunakis. eds., *Methods in Enzymology*, 92:168–174, Academic Press [1983]). Polystyrene 96-well microtiter plates were coated overnight at room temperature with 50 μl per well of a 1 μg/ml HCV antigen solution in PBS. Any remaining binding sites on the polystyrene wells were blocked with 3% bovine serum albumin (BSA) (Intergen, Purchase, N.Y.) in PBS for 30 minutes at room temperature. Plates were washed three times with distilled water. Fifty microliters of hybridoma tissue culture supernatants were incubated for 1 hour at room temperature in the wells, and the wells were washed three times with distilled water. Antibody binding to antigen was detected using goat anti-mouse IgG+M-horseradish peroxidase (HRPO) (Kirkegaard-Perry Laboratories [KPL], Gaithersburg, Md.) diluted at a concentration of 1:1000 in the block solution and incubated 30 minutes at room temperature. The plates were washed with distilled water and o-phenylenediamine substrate (OPD; Abbott Laboratories, Abbott Park, Ill.) was used as the chromogen. Plates were read at 492 nm. Hybrid cultures were regarded as potential HCV antibody-positive when the optical density (OD) was 3 times the negative control (NC) and significant preferential to the HCV antigen plate was observed compared to antibody binding of the irrelevant antigen coated plate, i.e.: >0.2 OD difference and <0.2 OD signal on the latter.

E. Western Blot

Hybrid antibody specificity was confirmed with Western blot analysis (Towbin & Gordon. *J. Immunol. Methods*, 72:313–340 [1984]). HCV recombinant proteins and irrelevant proteins were electrophoresed by sodium dodecyl sulfate-polyacrylamide gel electrophoresis (SDS-PAGE) and then transferred to nitrocellulose, according to the manufacturer's instructions (Schleicher & Schuell, Keene, NH; Bio-Rad, Richmond, Calif.). The nitrocellulose strips were blocked with 1% bovine hemoglobin (Sigma Chemical Co., St. Louis, Mo.) and 0.5% Tween-20 (Fisher Scientific, Pittsburgh, Pa.) in PBS for 30 minutes at room temperature, then the strips were incubated with hybrid tissue culture supernatant. The strips were then washed in PBS and goat anti-mouse IgG+M-HRPO (KPL) added for 30 minutes. Antibody binding to the HCV antigen was visualized with 4-chloro-1-naphthol (Sigma) as the chromogenic substrate. Hybrid cultures were cloned and placed in cryostorage if HCV antibody specificity was demonstrated.

F. Establishment of Clones

HCV specific hybrids were cloned by limiting dilution (Goding, *Monoclonal Antibodies: Principles and Practices*, 2nd ed., Academic Press, New York [1986]). Modifications included plating of the cultures in $\log_{10}$ dilution series and selecting positive clones for expansion from plates which exhibit <20% growth per 96 well tissue culture plate. Culture supernatants were tested after 10 days using the EIA and Western blot procedures described above. The selected clones were expanded for further evaluation and cryostoraged in 80% IMDM with 10% FBS and 10% DMSO (Sigma).

G. Monoclonal Antibody Isotype

Monoclonal antibody isotype was determined with the SBA Clonotyping System III kit (Southern Biotechnology Associates, Inc., Birmingham, Ala) with modifications. EIA 96-well microtiter plates were coated overnight at room temperature with 100 μl/well of a 1:1000 dilution of goat anti-mouse IgG+M (H+L) (KPL). Plates were blocked for 30 minutes with 3% BSA in PBS and washed with water. Culture samples were added to the wells, incubated for 1 hour, and washed with water. The kit's goat anti-mouse subtype specific conjugates were added for a 30 minute incubation period. Following a water wash, color was identified with OPD substrate. The goat anti-mouse isotype specific conjugate that bound to the mouse immunoglobin and displayed a >0.1 OD at 492 nm signaled the subtype.

H. Monoclonal Antibody Production

Clones selected for further evaluation were scaled up in tissue culture T-flasks and $10^6$ cells were injected into the peritoneal cavity of pre-pristaned BALB/c mice (Charles River Biotechnical Services, Inc., Wilmington, Mass.) (see Hurrell, supra). The resulting ascites fluid was harvested 7–10 days after injection, centrifuged, and stored at −20° C. The IgG antibody was affinity purified on Protein A (Pharmacia-LKB Biotechnologies, Piscataway, N.J.) utilizing the automated OROS purification system Model 100 (see Goding, supra, for basic principles). The IgM antibodies were purified by molecular sizing on a S-300 column (Pharmacia-LKB).

All the following characterization information was performed with purified monoclonal antibody.

I. Isoelectric Focusing (IEF)

A cell line quality control to ensure consistency of frozen lots included measuring the antibody pI point on an IEF gel apparatus (Bio-Rad) which separates proteins based on net charge. Briefly, a bis-acrylamide-riboflavin solution was applied to an acrylamide gel, exposed to fluorescent lighting for 1 hour, then stored overnight at 4° C. A 1 μg sample of monoclonal antibody and standards were laid upon the gel and electrophoresed over a 1–2 hour period. Following a series of fixatives and washes, the gel was silver stained (Bio-Rad). The pI value of the monoclonal antibody was calculated by migratory distance through the gel and was directly compared to the protein standards' migratory distance of known pI values. The distinctive finger print banding pattern reflected the pI microheterogeneity between independently produced lots of antibody (Hamilton, R. G., Reimer, C. B., Rodkey, L. S. (1987) Quality control of murine monoclonal antibodies using isoelectric focusing affinity immunoblot analysis. *Hybridoma* 6:205–217).

J. EIA and Western Blot Specificity of Monoclonal Antibodies

All monoclonal antibodies noted herein were screened on an assortment of available recombinant HCV antigens as disclosed in U.S. patent application Ser. No. 07/572,822 entitled HEPATITIS C ASSAY UTILIZING RECOMBINANT PROTEINS, which enjoys common ownership and in incorporated herein by reference. The procedures are outlined above. The multiple antigen screening technique confirmed the HCV specificity and to exclude the HCV non-specific CKS, λPL, or linker-arm reactivity of the monoclonal antibodies.

K. EIA Epitope Competition Studies

To investigate specificity and antigen binding distinctions, epitope grouping experiments were performed utilizing biotin labeled and unlabeled monoclonal antibodies (Langone & Van Vunakis, *Methods in Enzymology*, 92:242–253, Academic Press [1983]). Briefly, the antibodies were labeled with NHS-LC-biotin (Pierce Chemical Co., Rockford, Ill.) according to the manufacturer's instructions. Microtiter wells were coated with the immunogen as previously described. First, $\log_2$ dilutions of the unlabeled antibody were pre-incubated in the wells for 15 minutes, followed by the addition of a fixed amount of biotinylated antibody (the dilution in a direct EIA of the biotinylated antibody alone which gave a value of 50% of the maximum absorbance value) and incubated for 20 minutes. Plates were washed three times with water. Diluted streptavidin-HRPO (Zymed, South San Francisco, Calif.) was added to the wells and incubated for 30 minutes. The plates were washed again and OPD color developed as previously described. The absorbance was read at 492 nm. Antibodies of the same or related epitope had signal blocked or inhibited by >50%. No inhibition was observed with antibodies of distinct specificity. This was performed reciprocally for antibodies produced within HCV core region.

L. RIA Reciprocal Competition

Beads coated with the appropriate antigen or peptide were incubated with 100 μl of unlabeled monoclonal antibody diluted into recalcified negative human plasma (NHP, testing negative for anti-HCV, anti-HIV and HBsAg) at monoclonal antibody concentrations of 1–20 μg/ml. 100 μl of radiolabeled antibody at 1 to 4 μCi/ml diluted into HTLV I kit specimen diluent (containing detergent, animal sera, buffer) was incubated with the bead for 2 hours at 45° C. or 18–20 hours at 20°–25° C. Beads were washed and counted for radioactivity.

M. EIA Reactivity with Synthetic Peptides

Beads coated with 3 mg/ml were incubated with 100 ml of monoclonal antibody at concentrations of 0.02–1 mg/ml for 1 hour. The beads were washed and goat anti-mouse IgG+M-HRPO (KPL) was added for 30 minutes. The beads were washed again and OPD (Abbott Labs) was used as the chromagen for O.D. readings at 492 nm.

N. HCV Antigen Assays

Beads coated with one or a cocktail of anti-HCV monoclonal antibody were incubated with 200 μl of specimen for 2 hours at 40°–45° C. or 18–20 hours at 20°–25° C. Beads were washed with distilled water and then incubated with 200 μl of radiolabeled anti-HCV monoclonal antibody (one or more) for 2 hours at 45° C. Beads were washed and counted in a gamma counter.

O. Characterization of Monoclonal Antibody

Monoclonal antibody against the HCV CORE domain (1-75) fell into two distinct groups based on reciprocal competitive studies. All groups reacted with CKS-CORE (1-150) and IPL-core, IPL-33c-core and synthetic peptides corresponding to (1-75). Group 1 monoclonal antibody 13-975-157 strongly reacted with peptide (1-75), somewhat to (35-75), and not to (35-61). Group 2 monoclonal antibody 14-153-234 clearly reacted to peptides (1-75) and (35-75), but not to (35-61). Unlike the other groups, monoclonal antibody 14-1350-210, reacted strongly to all 3 of the HCV core synthetic peptides. These data are shown in Tables 5 and 6.

ability of anti-HCV positive human specimens to compete either group 2 monoclonal antibody (14-153) or group 3 monoclonal antibody (14-1350) for binding to λPL-CORE coated beads (1 μg/ml) was determined. Ten anti-HCV reactive specimens and two anti-HCV negative specimens were tested. Specimens giving greater than 50% inhibition of the binding signal were considered reactive for anti-CORE antibody. Seven of 10 positive specimens competed with group 2 (14-153) and 100% (10/10) competed with group 3 (14-1350). These data suggest that infected individuals vary in the antibody response to different HCV CORE epitopes.

TABLE 5

Reactivity on Western Blot

| Cell lline | CKS-core | λPl core | λPl-c33-core | CKS-c33 | CKS-C33-BCD | CKS-BCD | CKS-B | CKS-E | CKS | SOD 100 | CKS-A'BCD | CKS-A"BCD |
|---|---|---|---|---|---|---|---|---|---|---|---|---|
| 13-975-157 | + | + | + | − | − | − | − | − | − | − | − | − |
| 14-153-234 | + | + | + | − | − | − | − | − | − | − | − | − |
| 14-1350-210 | + | + | + | − | − | − | − | − | − | − | − | − |

TABLE 6

Reactivity on EIA

| Group | Cell Line | pI | Isotype | CKS-core | λPL-core | λPL-33c-core | CKS-33c | CKS-33c-BCD | HCV-core Synthetic Peptide 1-75 | 35-75 | 35-61 |
|---|---|---|---|---|---|---|---|---|---|---|---|
| 1 | 13-975-157 |   | IgM k | + | + | + | − | − | + | +/− | − |
| 2 | 14-153-234 | 6 | IgG2a k + | + | + | − | − | − | + | + | − |
| 3 | 14-1350-210 |   | IgM k | + | + | + | − | − | + | + | + |

Example 10

Anti-CORE Immunoassays

Data from one step competitive anti-CORE assay, performed as described hereinabove for "RIA Reciprocal Competition" is shown in Table 7. In these experiments, the

TABLE 7

Competitive One step anti-CORE assay

| | Label: 14-153-234 | | | | | Label: 14-1350-210 | | | | |
|---|---|---|---|---|---|---|---|---|---|---|
| Specimen | CPM | AVG | S/N | % Inhib | Result | CPM | AVG | S/N | % Inhibition | Result |
| NC | 48272 47010 50345 | 48542 | | | | 36866 | 34521 35655 31041 | | | |
| Elevated ALT | | | | | | | | | | |
| 27 | 4845 5414 | 5130 | 0.11 | 89.4 | + | 440 370 | 405 | 0.01 | 98.8 | + |
| 238-NC | 40035 43892 | 41964 | 0.86 | 13.6 | − | 28481 28106 | 28294 | 0.82 | 18.8 | − |
| 135 | 620 496 | 558 | 0.01 | 98.9 | + | 114 119 | 117 | 0.00 | 99.7 | + |
| 163 | 14540 16402 | 15471 | 0.32 | 68.1 | + | 100 104 | 102 | 0.00 | 99.6 | + |
| 173 | 5344 5717 | 5531 | 0.11 | 88.6 | + | 114 137 | 126 | 0.00 | 99.6 | + |
| 220 | 1049 | 1012 | 0.02 | 97.6 | + | 124 | 130 | 0.00 | 99.6 | + |

TABLE 7-continued

Competitive One step anti-CORE assay

| Specimen | Label: 14-153-234 | | | | | Label: 14-1350-210 | | | | |
|---|---|---|---|---|---|---|---|---|---|---|
| | CPM | AVG | S/N | % Inhib | Result | CPM | AVG | S/N | % Inhibition | Result |
| | 974 | | | | | | 136 | | | |
| 252 | 231 | 212 | 0.00 | 99.6 | + | 138 | 135 | 0.00 | 99.6 | + |
| | 192 | | | | | | 132 | | | |
| R13203 | 56075 | 55778 | 1.15 | −14.9 | − | 3029 | 3479 | 0.10 | 89.9 | + |
| | 55480 | | | | | | 3929 | | | |
| SAC190 | 472 | 417 | 0.01 | 99.1 | + | 102 | 194 | 0.01 | 99.4 | + |
| | 362 | | | | | | 284 | | | |
| 7088396 | 41692 | 41963 | 0.86 | 13.6 | − | 102 | 122 | 0.00 | 99.6 | + |
| | 42233 | | | | | | 142 | | | |
| EP10968 | 39418 | 40470 | 0.83 | 16.6 | − | 94 | 95 | 0.00 | 99.7 | + |
| | 41522 | | | | | | 95 | | | |
| 14-153 | 5580 | 5491 | 0.11 | 88.7 | + | 16216 | 14178 | 0.41 | 58.9 | + |
| | 5402 | | | | | | 12140 | | | |
| 283-NC | 45170 | 44219 | 0.91 | 8.9 | − | 24748 | 23908 | 0.69 | 30.7 | − |
| | 43268 | | | | | | 23067 | | | |

Example 11

Anti-HCV CORE Two-Step Blocking Assay

A two step blocking assay performed according to a competitive one-step assay described herein for "RIA Reciprocal Competition" for detection of anti-HCV CORE, using labeled group 3 monoclonal antibody (14-1350-210), is shown in Table 8. Sixteen specimens which were repeat reactive for anti-C100 (using the Ortho 1.0 gen kit, available from Ortho Diagnostics, Raritan, N.J.) were tested. Six had been shown to be false positive by an anti-C100 confirmatory assay and 10 were confirmed as positive. None of the six false positives gave greater than 20% inhibition in the assay compared to 48–99% inhibition observed for true anti-C100 positives in this anti-CORE assay.

TABLE 8

Two Step Blocking Anti-HCV-CORE Assay
Bead: 1.0 µg IPL-CORE; Label: 14-1350 in HTLV I diluent

| Specimen | CPM | AVG | S/N | % Inhibition | Result |
|---|---|---|---|---|---|
| NC | 23376 | 25969 | | | |
| | 26257 | | | | |
| | 28275 | | | | |
| Sacramento Negative 1.0 Gen. | | | | | |
| 183 | 31956 | | 1.23 | −23.1 | − |
| 184 | 26525 | | 1.02 | −2.1 | − |
| 185 | 24714 | | 0.95 | 4.8 | − |
| 192 | 20664 | | 0.80 | 20.4 | − |
| 193 | 20934 | | 0.81 | 19.4 | − |
| 194 | 23321 | | 0.90 | 10.2 | − |
| Sacramento Positive 1.0 Gen. | | | | | |
| 188 | 13569 | | 0.52 | 47.7 | + |
| 189 | 2243 | | 0.09 | 91.4 | + |
| 191 | 2361 | | 0.09 | 90.9 | + |
| 195 | 284 | | 0.01 | 98.9 | + |
| 196 | 170 | | 0.01 | 99.3 | + |
| 197 | 487 | | 0.02 | 98.1 | + |
| 206 | 3639 | | 0.14 | 86.0 | + |
| 207 | 2713 | | 0.10 | 89.6 | + |
| 208 | 145 | | 0.01 | 99.4 | + |
| 214 | 10398 | | 0.40 | 60.0 | + |

Example 12

HCV CORE Ag Assay

Results from one type of CORE Ag assay is shown in Table 9. This assay was performed as a 2 step assay according to the procedure outlined hereinabove in "HCV Antigen Assay" and as follows: The first incubation with specimen (200 µl) was 18 hours at room temperature, followed by 2 hr. incubation at 45° C. with radiolabeled group 2 monoclonal antibody 14-153. Since the bead was coated with a group 3 monoclonal antibody 14-1350 which does not compete with group 2, a one step sandwich assay was also possible.

Specimens giving S/N values greater than 3.0 were considered reactive for CORE Ag. Sensitivity of the assay with recombinant λPL-CORE was about 100 ng/ml. Two of 13 specimens from patients with elevated ALT and anti-C-100 reactivity were considered reactive for CORE antigen.

TABLE 9

HCV CORE Ag Assay
(14-1350 bead/14-153 label)

| | Specimen | CPM | Average | S/N | Result |
|---|---|---|---|---|---|
| | NC | 114 | 128 | | |
| | | 137 | | | |
| | | 133 | | | |
| λPL-CORE | 110 µg/ml | 1846 | 1822 | 14.23 | + |
| | | 1798 | | | |
| " | 11 µg/ml | 1488 | 1447 | 11.30 | + |
| | | 1405 | | | |
| " | 1.1 µg/ml | 1220 | 1246 | 9.73 | + |
| | | 1271 | | | |
| " | 110 ng/ml | 514 | 472 | 3.69 | + |
| | | 430 | | | |
| " | 11 ng/ml | 182 | 175 | 1.36 | − |
| | | 167 | | | |
| Elevated ALT | 10 | 206 | 212 | 1.65 | − |
| | | 217 | | | |
| " | 27 | 160 | 174 | 1.36 | − |
| | | 187 | | | |
| " | 54 | 710 | 628 | 4.91 | + |
| | | 546 | | | |
| " | 77 | 454 | 458 | 3.57 | + |
| | | 461 | | | |
| " | 135 | 160 | 189 | 1.48 | − |
| | | 218 | | | |

TABLE 9-continued

HCV CORE Ag Assay
(14-1350 bead/14-153 label)

| Specimen | CPM | Average | S/N | Result |
|---|---|---|---|---|
| " | 163 | 323 | 328 | 2.56 | — |
|   |   | 332 |   |   |   |
| " | 173 | 346 | 342 | 2.67 | — |
|   |   | 337 |   |   |   |
| " | 220 | 274 | 275 | 2.14 | — |
|   |   | 275 |   |   |   |
| " | 238 | 157 | 171 | 1.34 | — |
|   |   | 185 |   |   |   |
| " | 252 | 227 | 216 | 1.68 | — |
|   |   | 204 |   |   |   |
| " | 283 | 194 | 175 | 1.36 | — |
|   |   | 155 |   |   |   |
| " | 28 | 258 | 226 | 1.77 | — |
|   |   | 194 |   |   |   |
| " | 290 | 162 | 175 | 1.36 | — |
|   |   | 187 |   |   |   |

Example 13

HCV Antibody Test Employing Cocktails of Monoclonal Antibodies

Also performed was a similar CORE Antigen format using a cocktail of anti-CORE monoclonal antibody on the solid phase and in label (14-1350-210, 14-153-234, and 14-726). In twenty five anti-C-100 repeat reactive specimens, one specimen (SAC 161) was significantly elevated in reactivity. A frequency histogram of a negative anti-HCV population from the Interstate Blood Bank was prepared (not shown). A cutoff set at S/N=2.0 gave 5 standard deviations from the negative population mean. No negative specimen gave S/N>1.6.

Example 14

Production and use of cell lines 16-296-534, 6-914-518 and 6-1070-110

A. Production of recombinant HCV antigens and immunogens

Recombinant antigens were made as fusion proteins with CMP-XDO synthetase in *E. coli* according to methods known to those in the art, or as non fused protein with λPL promoter system. The following proteins were cloned and purified:

| λPL CORE | (1–150) |
| CKS-CORE | (1–150) |
| CKS-33c | (1191–1457) |
| λPL-33c-CORE | (fusion of 1191–1457 and 1–150) |
| CKS-BCD | (156–1930) |
| CKS-E | (1931–2189) (NS4/NS5 reaction) |
| CKS-B | (1676–1790) |

See FIG. 1B for map of HCV genome and approximate locations of HCV regions. Recombinant protein C-100 (1569–1930) was obtained from Chiron as a fusion protein with superoxide dismutase (SOD). All recombinant proteins were greater than 90% pure by SDS-PAGE.

B. Immunization of Mice

BALB/c mice (Charles River Laboratories, Charles River, N.Y.), 6–8 weeks old, were initially immunized subcutaneously and intraperitoneally with 10–100 µg of the HCV CKS-33C in 100 µl of Freund's complete adjuvant (Difco, Detroit, Mich.). On day 14, a second similar boost was administered with the immunogen emulsified in incomplete Freund's adjuvant (Difco). On day 25, 10–100 µg of the immunogen was diluted into 100 µl of phosphate buffered saline (PBS), pH 7.2, and injected intravenously into the tail vein (J. Goding, *Monoclonal Antibodies: Principles and Practice* [New York; Academic Press, 1986]). Sera titers were not evaluated.

C. Fusion

On day 28, mice were sacrificed and splenocytes were fused in a 1:1 ratio with the SP2/0 myeloma line according to known conventional methods (G. Kohler and C. Milstein, *Nature* (1975) 256:495–497; J. Goding, supra). The cell fusion pellet was dispersed with 1 ml 50% polyethylene glycol (PEG) (American Type Culture Collection, MW 1450) and centrifuged in Iscove's Modified Dulbecco's Medium (IMDM) (Gibco, Grand Island, N.Y.). The cells were resuspended in HAT (hypoxanthine-aminopterin-thymidine)-selective IMDM with 10% fetal bovine serum (FBS) (Hyclone Laboratories, Logan, Utah) and plated at $3\times10^5$ cells per 96-well tissue culture plates. Growth promoters included in the HAT media were 0.5% STM (RIBI Immunochem Research, Inc., Hamilton, Mont.) and 1% Origen Hybridoma Cloning Factor (Igen, Rockville, Md.). Growth medium was replaced in culture wells post-fusion on day 5 and 7 using HT (hypoxanthine-thymidine) supplemented IMDM with 10% FBS.

D. Enzyme Immunoassay (EIA)

Culture supernatants were EIA screened 10 days post-fusion against the immunizing antigen to detect hybrids secreting HCV specific antibody and a non-specific protein to eliminate any false positives (Langone & Van Vunakis, eds., *Methods in Enzymology*, 92:168–174, Academic Press [1983]). Polystyrene 96-well microtiter plates were coated overnight at room temperature with 100 µl per well of a 1 µg/ml HCV antigen solution in PBS. Any remaining binding sites on the polystyrene wells were blocked with 3% bovine serum albumin (BSA) (Intergen, Purchase, N.Y.) in PBS for 30 minutes at room temperature. Plates were washed three times with distilled water. Fifty microliters of hybridoma tissue culture supernatants were incubated for 1 hour at room temperature in the wells, and the wells were washed three times with distilled water. Antibody binding to antigen was detected using goat anti-mouse IgG+M-horseradish peroxidase (HRPO) (Kirkegaard-Perry Laboratories [KPL], Gaithersburg, Md.) diluted at a concentration of 1:1000 in the block solution and incubated 30 minutes at room temperature. The plates were washed with distilled water and o-phenylenediamine substrate (OPD; Abbott Laboratories, Abbott Park, Ill.) was used as the chromogen. Plates were read at 492 nm. Hybrid cultures were regarded as potential HCV antibody-positive when the optical density (OD) was 3 times the negative control (NC) and significant preferential to the HCV antigen plate was observed compared to antibody binding of the irrelevant antigen coated plate, i.e.: >0.2 OD difference and <0.2 OD signal on the latter.

E. Western Blot

Hybrid antibody specificity was confirmed with Western blot analysis (Towbin & Gordon, J. Immunol. Methods, 72:313–340 [1984]). HCV recombinant proteins and irrelevant proteins were electrophoresed by sodium dodecyl sulfate-polyacrylamide gel electrophoresis (SDS-PAGE) and then transferred to nitrocellulose, according to the manufacturer's instructions (Schleicher & Schuell, Keene, NH; Bio-Rad, Richmond, Calif.). The nitrocellulose strips were blocked with 1% bovine hemoglobin (Sigma Chemical Co., St. Louis, Mo.) and 0.5% Tween-20 (Fisher Scientific, Pittsburgh, Pa.) in PBS for 30 minutes at room temperature, then the strips were incubated with hybrid tissue culture supernatant. The strips were then washed in PBS and goat anti-mouse IgG+M-HRPO (KPL) added for 30 minutes. Antibody binding to the HCV antigen was visualized with 4-chloro-1-naphthol (Sigma) as the chromogenic substrate. Hybrid cultures were cloned and placed in cryostorage if HCV antibody specificity was demonstrated.

F. Establishment of Clones

HCV specific hybrids were cloned by limiting dilution (Goding, *Monoclonal Antibodies: Principles and Practices*, 2nd ed, Academic Press, New York [1986]). Modifications included plating of the cultures in $log_{10}$ dilution series and selecting positive clones for expansion from plates which exhibit <20% growth per 96 well tissue culture plate. Culture supernatants were tested after 10 days using the EIA and Western blot procedures described above. The selected clones were expanded for further evaluation and cryostoraged in 80% IMDM with 10% FBS and 10% DMSO (Sigma).

G. Monoclonal Antibody Isotype

Monoclonal antibody isotype was determined with the SBA Clonotyping System III kit (Southern Biotechnology Associates, Inc., Birmingham, Ala.) with modifications. EIA 96-well microtiter plates were coated overnight at room temperature with 100 µl/well of a 1:1000 dilution of goat anti-mouse IgG+M (H+L) (KPL). Plates were blocked for 30 minutes with 3% BSA in PBS and washed with water. Culture samples were added to the wells, incubated for 1 hour, and washed with water. The kit's goat anti-mouse subtype specific conjugates were added for a 30 minute incubation period. Following a water wash, color was identified with OPD substrate. The goat anti-mouse isotype specific conjugate that bound to the mouse immunoglobin and displayed a >0.1 OD at 492 nm signaled the subtype.

H. Monoclonal Antibody Production

Clones selected for further evaluation were scaled up in tissue culture T-flasks and $10^6$ cells were injected into the peritoneal cavity of pre-pristaned BALB/c mice (Charles River Biotechnical Services, Inc., Wilmington, Mass.) (see Hurrell, supra). The resulting ascites fluid was harvested 7–10 days after injection, centrifuged, and stored at –20° C. The IgG antibody was affinity purified on Protein A (Pharmacia-LKB Biotechnologies, Piscataway, N.J.) utilizing the automated OROS purification system Model 100 (see Goding, supra, for basic principles). The IgM antibodies were purified by molecular sizing on a S-300 column (Pharmacia-LKB).

All the following characterization information was performed with purified monoclonal antibody.

I. Isoelectric Focusing (IEF)

A cell line quality control to ensure consistency of frozen lots included measuring the antibody pI point on an IEF gel apparatus (Bio-Rad) which separates proteins based on net charge. Briefly, a bis-acrylamide-riboflavin solution was applied to an acrylamide gel, exposed to fluorescent lighting for 1 hour, then stored overnight at 4° C. A 1 µg sample of monoclonal antibody and standards were laid upon the gel and electrophoresed over a 1–2 hour period. Following a series of fixatives and washes, the gel was silver stained (Bio-Rad). The pI value of the monoclonal antibody was calculated by migratory distance through the gel and was directly compared to the protein standards' migratory distance of known pI values. The distinctive finger print banding pattern reflected the pI microheterogeneity between independently produced lots of antibody (Hamilton, R. G., Reimer, C. B., Rodkey, L. S. (1987) Quality control of murine monoclonal antibodies using isoelectric focusing affinity immunoblot analysis. *Hybridoma* 6:205–217).

J. EIA and Western Blot Specificity of Monoclonal Antibodies

All monoclonal antibodies noted herein were screened on an assortment of available recombinant HCV antigens as disclosed in U.S. patent application Ser. No. 07/572,822 entitled HEPATITIS C ASSAY UTILIZING RECOMBINANT PROTEINS, which enjoys common ownership and is incorporated herein by reference. The procedures are outlined above. The multiple antigen screening technique confirmed the HCV specificity and to exclude the HCV non-specific CKS, IPL, or linker-arm reactivity of the monoclonal antibodies.

K. EIA Epitope Competition Studies

To investigate specificity and antigen binding distinctions, epitope grouping experiments were performed utilizing biotin labeled and unlabeled monoclonal antibodies (Langone & Van Vunakis, *Methods in Enzymology*, 92:242–253, Academic Press [1983]). Briefly, the antibodies were labeled with NHS-LC-biotin (Pierce Chemical Co., Rockford, Ill.) according to the manufacturer's instructions. Microtiter wells were coated with the immunogen as previously described. First, $log_2$ dilutions of the unlabeled antibody were pre-incubated in the wells for 15 minutes, followed by the addition of a fixed amount of biotinylated antibody (the dilution in a direct EIA of the biotinylated antibody alone which gave a value of 50% of the maximum absorbance value) and incubated for 20 minutes. Plates were washed three times with water. Diluted streptavidin-HRPO (Zymed, South San Francisco, Calif.) was added to the wells and incubated for 30 minutes. The plates were washed again and OPD color developed as previously described. The absorbance was read at 492 nm. Antibodies of the same or related epitope had signal blocked or inhibited by >50%. No inhibition was observed with antibodies of distinct specificity. This was performed reciprocally for antibodies produced within HCV core region.

L. RIA Reciprocal Competition

Beads coated with the appropriate antigen or peptide were incubated with 100 µl of unlabeled monoclonal antibody diluted into recalcified negative human plasma (NHP, testing negative for anti-HCV, anti-HIV and HBsAg) at monoclonal antibody concentrations of 1–20 µg/ml. 100 µl of radiolabeled antibody at 1 to 4 µCi/ml diluted into HTLV I kit specimen diluent (containing detergent, animal sera, buffer, available from Abbott Laboratories, Abbott Park, Ill.) was incubated with the bead for 2 hours at 45° C. or 18–20 hours at 20°–25° C. Beads were washed and counted for radioactivity.

M. HCV Antigen Assays

Beads coated with one or a cocktail of anti-HCV monoclonal antibody were incubated with 200 µl of specimen for 2 hours at 40°–45° C. or 18–20 hours at 20°–25° C. Beads were washed with distilled water and then incubated with 200 µl of radiolabeled anti-HCV monoclonal antibody (one or more) for 2 hours at 45° C. Beads were washed and counted in a gamma counter.

N. Characterization of Monoclonal Antibody

Two monoclonal antibody competition groups against the HCV 33c region (1191–1457) are found in Table 10. The groups reacted with HCV CKS-33c, CKS-33c-CORE, and λPL-33c-CORE fusion proteins.

TABLE 10

Anti-HCV-33c Monoclonal Antibodies
EIA and Western Blot Reactivity
Recombinant HCV Antigen Reactivity

| Group # | Cell Line | pI | Isotype | CKS-core | λPL-core | λPL-33c-core | CKS-33c | CKS-33c-BCD | CKS-BCD | CKS-B | CKS |
|---|---|---|---|---|---|---|---|---|---|---|---|
| 1 | 6-296-534 | 6.0 | IgG1 k | − | − | + | + | + | − | − | − |
| 2 | 6-914-518 |  | IgG2b k | − | − | + | + | + | − | − | − |

Example 15

Anti-HCV-33c Competitive Assay

A one step competitive assay was developed using CKS-33c coated beads (0.1 µg/ml coating) and radiolabeled group 1 (6-296-534) and group 2 (6-914-518) monoclonal antibody for detection. Seven anti-C100 false positive sera samples and ten anti-C100 true positive sera samples obtained from the Interstate Blood Bank were tested using the two anti-33c monoclonal antibodies of the invention (Table 2). The false positive specimens gave no more than 25% inhibition for any of the monoclonal antibodies. Binding of monoclonal antibody 6-296-534 was almost completely inhibited by the anti-C100 positive specimen (84–100%). Interestingly, these specimens were not able to effectively compete group 2 monoclonal antibody for binding to 33c (0–24% inhibition).

Subclones of Table 11 hybrids have been established demonstrating comparable reactivity by EIA and RIA competitive binding studies.

TABLE 11

Competitive anti-HCV 33c Assays

| Specimen | CPM | AVG | S/N | % Inhib. | Result |
|---|---|---|---|---|---|
| Label: 6-296 in HTLV I diluent | | | | | |
| NC | 72473 | 70641 | | | |
|  | 67993 | | | | |
|  | 71456 | | | | |
| Sacramento negative specimens | | | | | |
| 145 | 55325 | | 0.78 | 21.7 | − |
| 146 | 65197 | | 0.92 | 7.7 | − |
| 148 | 53705 | | 0.76 | 24.0 | − |
| 149 | 57741 | | 0.82 | 18.3 | − |
| 151 | 89301 | | 1.26 | −26.4 | − |
| 152 | 88711 | | 1.26 | −25.6 | − |
| 154 | 67721 | | 0.96 | 4.1 | − |
| Sacramento positive specimens | | | | | |
| 147 | 5366 | | 0.08 | 92.4 | + |
| 150 | 3351 | | 0.05 | 95.3 | + |
| 153 | 240 | | 0.00 | 99.7 | + |
| 156 | 128 | | 0.00 | 99.8 | + |
| 159 | 3045 | | 0.04 | 95.7 | + |
| 160 | 47 | | 0.00 | 99.9 | + |
| 161 | 11276 | | 0.16 | 84.0 | + |
| 163 | 42 | | 0.00 | 99.9 | + |
| 165 | 1076 | | 0.02 | 98.5 | + |
| 167 | 66 | | 0.00 | 99.9 | + |
| Label: 6-914 in HTLV I diluent | | | | | |
| NC | 32156 | 34010 | | | |
|  | 34431 | | | | |

TABLE 11-continued

Competitive anti-HCV 33c Assays

| Specimen | CPM | AVG | S/N | % Inhib. | Result |
|---|---|---|---|---|---|
|  | 35444 | | | | |
| Sacramento negative specimens | | | | | |
| 145 | 38613 | | 1.14 | −13.5 | − |
| 146 | 36134 | | 1.06 | −6.2 | − |
| 148 | 35130 | | 1.03 | −3.3 | − |
| 149 | 30137 | | 0.89 | 11.4 | − |
| 151 | 36794 | | 1.08 | −8.2 | − |
| 152 | 30860 | | 0.91 | 9.3 | − |
| 154 | 34493 | | 1.01 | −1.4 | − |
| Sacramento positive specimens | | | | | |
| 147 | 29573 | | 0.87 | 13.0 | − |
| 150 | 34219 | | 1.01 | −0.6 | − |
| 153 | 28002 | | 0.82 | 17.7 | − |
| 156 | 31866 | | 0.94 | 6.3 | − |
| 159 | 32633 | | 0.96 | 4.0 | − |
| 160 | 30984 | | 0.91 | 8.9 | − |
| 161 | 34569 | | 1.02 | −1.6 | − |
| 163 | 27479 | | 0.81 | 19.2 | − |
| 165 | 25865 | | 0.76 | 23.9 | − |

Example 16

HCV-33c Antigen Assay

Results from a two step 33c antigen RIA assay are shown in Table 12. Assay specimens which gave S/N values greater than 4.0 were considered reactive. The assay was able to detect CKS-33c and IPL-33c-CORE at 300 ng/ml and 2.0 µg/ml respectively. Two of seven specimens from patients with elevated ALT and anti-C-100 were reactive for 33c antigen.

TABLE 12

HCV-33c Ag Assay
(6-914-518 bead/6-296-534, 6-1070-110 label)

| Specimen |  | CPM | Average | S/N | Result |
|---|---|---|---|---|---|
| NC |  | 327 | 312 | | |
|  |  | 287 | | | |
|  |  | 322 | | | |
| CKS-33c | 36 µg/ml | 17439 | 18125 | 58.09 | + |
|  |  | 18810 | | | |
| " | 3.6 µg/ml | 5256 | 5133 | 16.45 | + |
|  |  | 5010 | | | |
| " | 360 ng/ml | 1401 | 1340 | 4.29 | + |
|  |  | 1279 | | | |
| " | 36 ng/ml | 408 | 412 | 1.32 | − |
|  |  | 415 | | | |

TABLE 12-continued

HCV-33c Ag Assay
(6-914-518 bead/6-296-534, 6-1070-110 label)

| Specimen | | CPM | Average | S/N | Result |
|---|---|---|---|---|---|
| " | 3.6 ng/ml | 305 | 321 | 1.03 | − |
| | | 336 | | | |
| IPL-33c-CORE | 248 µg/ml | 5832 | 5873 | 18.82 | + |
| | | 5913 | | | |
| " | 24.8 µg/ml | 3607 | 3545 | 11.36 | + |
| | | 3483 | | | |
| " | 2.48 g/ml | 1261 | 1369 | 4.39 | + |
| | | 1476 | | | |
| " | 248 mg/ml | 455 | 471 | 1.51 | − |
| | | 487 | | | |
| " | 24.8 ng/ml | 310 | 331 | 1.06 | − |
| | | 352 | | | |
| Elevated ALT | 27 | 2239 | 1999 | 6.41 | + |
| | | 1759 | | | |
| " | 238 | 717 | 516 | 1.65 | − |
| | | 315 | | | |
| " | 173 | 679 | 748 | 2.40 | − |
| | | 817 | | | |
| " | 252 | 337 | 421 | 1.35 | − |
| | | 505 | | | |
| " | 283 | 377 | 383 | 1.23 | − |
| | | 389 | | | |
| " | 28 | 1311 | 1331 | 4.26 | + |
| | | 1350 | | | |
| " | 290 | 305 | 289 | 0.93 | − |
| | | 273 | | | |

Example 17

Monoclonal Antibodies As A Cocktail

A slightly different variation of the assay of Example 16 was performed. In this procedure, three anti-33c monoclonal antibodies (6-914-518, 6-296-534, and 6-1070-110) were coated onto beads and used as a cocktail in the label. None of the anti-C-100 repeat reactives or IBB negative population were reactive with all specimens, giving S/N values less than 1.7.

Thus, the novel monoclonal antibodies of the invention can be used in a variety of ways. These monoclonal antibodies can be used for immunoprecipitation of amplified product and detection of HCV nucleic acid microparticles or carrier (solid phase) coated with anti-HCV monoclonal antibody used to capture virus or viral protein associated with HCV RNA, which may be followed by detection methodology for RNA. An example of this type of assay is taught in pending U.S. patent application Ser. No. 07/568, 663, entitled A METHOD FOR AMPLIFYING AND DETECTING A TARGET NUCLEIC ACID SEQUENCE, which enjoys common ownership and is incorporated herein by reference.

These monoclonal antibodies also can be used for localization of HCV antigens within the cell using HCV monoclonal antibody tagged directly (fluorescence, colloidal gold, etc.) or using secondary tagged anti-mouse antibody. Histopathology of disease may be tracked. Further, the detection of native or recombinant HCV antigens in sera, tissue, cells, culture media, or body fluid using individual monoclonal antibodies in a sandwich configuration or a cocktail of monoclonal antibodies on the solid phase and in the detection system.

One step antigen assays using monoclonal antibodies against non overlapping epitopes may also be performed. Some monoclonal antibodies may recognize antigenic epitopes not recognized by the infected individual and therefore may be possible to recognize serum Ag both free and bound with human antibody. Furthermore, "cryptic" or hidden antigens or antigenic determinants may be uncovered by treatment of specimen with detergent or reducing agent or both. For example, CORE antigen may exist in a capsid form covered by the virus envelope. Stripping the envelope with detergent should expose CORE antigen. Monoclonal antibodies may also offer pragmatic advantages over high titer polyclonal antibody in giving greater sensitivity in assay or allowing shorter incubation times.

Further, antibody immunoassays, one or two step competitive assays, were developed in which anti-HCV competed with labeled anti-HCV monoclonal antibody for binding to a limited number of antigenic sites. A more sensitive competitive assay may be developed in which human anti-HCV binds to HCV Ag in solution blocking or inhibiting the HCV Ag binding in HCV Ag sandwich assay. Competitive assays using monoclonal antibodies allow a more precise mapping of human antibody epitopes and may be useful for determining virus neutralizing antibody epitopes. Some monoclonal antibodies may have virus neutralizing activity. Finally, monoclonal antibodies should be useful in immunoaffinity purification of native viral and recombinant HCV antigens and proteins.

The hybridomas which produce the monoclonal antibodies of the invention are identified as hybridoma H81C17 producing monoclonal antibody H81C17, hybridoma H35C54 producing monoclonal antibody H35C54, hybridoma H28C110 producing monoclonal antibody H28C110, hybridoma H4C20 producing monoclonal antibody H4C20, hybridoma H11C130 producing monoclonal antibody H11C130 and hybridoma H1C46 producing monoclonal antibody H1C46. Hybridomas H28C110, H81C17 and H11C130 were deposited at the American Type Culture Collection, 12301 Parklawn Drive, Rockville, Md. 20852 as of Oct. 30, 1990, and have been accorded the following deposit numbers: H28C110 was accorded A.T.C.C. deposit No. HB 10587; H81C17 was accorded A.T.C.C. deposit No. HB10588 and H11C130 was accorded A.T.C.C. deposit No. HB 10589. Hybridomas H35C54, H4C20 and H1C46 were deposited at the American Type Culture Collection, 10231 Parklawn Drive, Rockville, Md. 20852 as of Oct. 31, 1990, and were accorded the following deposit numbers: H35C54 was accorded A.T.C.C. deposit No. HB 10592; H4C20 was accorded A.T.C.C. deposit No. HB 10593 and H1C46 was accorded A.T.C.C. deposit No. HB 10594.

Also, the hybridoma cell lines which produce the monoclonal antibodies of the invention are identified as hybridoma cell line 13-975-157 (producing monoclonal antibody 13-975-157 ), hybridoma cell line 14-153-234 (producing monoclonal antibody 14-153-234) and hybridoma cell line 14-1350-210 (producing monoclonal antibody 14-1350-210). These hybridoma cell lines were deposited at the American Type Culture Collection, 12301 Parklawn Drive, Rockville, Md. 20852 on Nov. 16, 1990 and were accorded the following deposit numbers: Hybridoma cell line 13-975-157 was accorded A.T.C.C. deposit No. HB 10608, hybridoma cell line 14-153-234 was accorded A.T.C.C. deposit No. HB 10604, and hybridoma cell line 14-1350-210 was accorded A.T.C.C. deposit No. HB 10602.

Further, the hybridoma cell lines which secrete the monoclonal antibodies of the invention are identified as hybridoma cell line 6-296-534 (secreting monoclonal antibody 6-296-534) and hybridoma cell line 6-914-518 (secreting hybridoma cell line 6-914-518). These hybridoma cell lines were deposited at the American Type Culture Collection, 12301 Parklawn Drive, Rockville, Md. 20852 on Nov. 16, 1990 and were accorded the following deposit numbers: Hybridoma cell line 6-296-534 was accorded A.T.C.C. deposit No. HB 10607, and hybridoma cell line 6-914-518 was accorded A.T.C.C. deposit No. HB 10600.

Other variations of applications of the use of the unique monoclonal antibodies provided herein include the detection of HCV antigen in immune complexes, or latent and/or cryptic antigens, and/or associated with viral nucleic acid for detection of the nucleic acid by PCR, LCR, or by direct hybridization. Still other variations and modifications of the specific embodiments of the invention as set forth herein will be apparent to those skilled in the art. Accordingly, the invention is intended to be limited only in accordance with the appended claims.

specifically bind to HCV proteins C-100 and 33C, and further wherein said monoclonal antibody is secreted by a hybridoma selected from the group consisting of A.T.C.C. deposit Nos. HB 10592, HB 10588, HB 10608, HB 10604 and HB 10602.

5. A hybridoma which produces a monoclonal antibody which specifically binds to Hepatitis C Virus (HCV) protein C-100 and does not specifically bind to HCV proteins 33C and CORE, wherein said hybridoma is selected from the group consisting of A.T.C.C. deposit Nos. HB 10593 and HB 10587.

6. A hybridoma which produces a monoclonal antibody which specifically binds to Hepatitis C Virus (HCV) protein 33C and does not specifically bind to HCV C-100 and HCV CORE proteins, wherein said hybridoma is selected from the

TABLE 1

CHARACTERIZATION OF MONCLONAL ANTIBODIES TO HCV PROTEINS

| MAB ID | Immunogen | Western Blot Reactivity[1] | | EIA Titer With Purified IgG[2] | | Isotype | Competition w/Immune Human Sera[3] | Epitope Specificity a.a. of HCV genome[4] |
|---|---|---|---|---|---|---|---|---|
| | | CKS fusion protein | λpL construct | CKS fusion protein ng/ml | λpL construct ng/ml | | | |
| H81C17 | pHCV34 (HCV-CORE) | +++ | +++ | 16 | 3.9 | IgG1, k | – | 1–150 |
| H35C54 | pHCV34 | +++ | ++ | 31 | 7.8 | IgG1, k | – | 1–150 |
| H28C110 | pHCV23 (HCV C-100) | +++ | +++ | 0.5 | 0.4 | IgG1, k | + | 1702–1709 |
| H4C20 | pHCV23 (HCV C-100) | +++ | +++ | 125 | 30 | IgG1, k | ++ | 1899–1930 |
| H11C130 | pHCV29 (HCV 33C) | +++ | +++ | 0.5 | 0.5 | IgG1, k | +++ | 1192–1339 |
| H1C46 | pHCV29 (HCV 33C) | +++ | + | 0.5 | 63 | IgG1, k | +++ | 1339–1457 |

[1]Data reflects the reactivity of one each monoclonal antibody with the respective immunogen expressed as (a) CKS fusion protein and (b) under λpL promoter without any fusion protein in E. coli. +++ indicates strong reactivity; + indicates weak reactivity.
[2]Data reflects the reactivity of each monoclonal with the immunogen as described in 1. The EIA Titer is defined as the concentration of the monoclonal IgG protein in ng/ml which will give the absorbance of 4 times the negative control at 492 nm.
[3]+++ indicates strong competition (>80%); + indicates weak competition (approximately 50%).
[4]Epitope specificity was determined based on several experiments as described in Examples 5 and 6.

We claim:

1. A monoclonal antibody which binds to HCV CORE protein and which does not compete with human sera containing antibodies to HCV CORE protein, secreted by a hybridoma selected from the group consisting of A.T.C.C. Deposit Nos. HB 10588 and HB 10592, wherein the monoclonal antibody produced by hybridoma HB 10588 binds to amino acids 1-150 of HCV, and the monoclonal antibody produced by hybridoma HB 10592 binds to amino acids 1-150 of HCV.

2. A monoclonal antibody or fragment thereof, wherein said monoclonal antibody or fragment specifically binds to Hepatitis C Virus (HCV) protein C-100 and does not specifically bind to HCV proteins 33C and CORE, and further wherein said monoclonal antibody is secreted by a hybridoma selected from the group consisting of A.T.C.C. deposit Nos. HB 10593 and HB 10587.

3. A monoclonal antibody or fragment thereof, wherein said monoclonal antibody or fragment specifically binds to Hepatitis C Virus (HCV) protein 33C and does not specifically bind to HCV proteins C-100 and CORE, and further wherein said monoclonal antibody is secreted by a hybridoma selected from the group consisting of A.T.C.C. deposit Nos. HB 10594, HB 10589, HB 10607 and HB 10600.

4. A monoclonal antibody or fragment thereof, wherein said monoclonal antibody or fragment specifically binds to Hepatitis C Virus (HCV) protein CORE and does not group consisting of A.T.C.C. deposit Nos. HB 10594, HB 10589, HB 10607 and HB 10600.

7. A hybridoma which produces a monoclonal antibody which specifically binds to Hepatitis C Virus (HCV) protein CORE and does not specifically bind to HCV C-100 and HCV CORE proteins, wherein said hybridoma is selected from the group consisting of A.T.C.C. deposit Nos. HB 10592, HB 10588, HB 10608, HB 10604 and HB 10602.

8. A method for determining the presence of Hepatitis C Virus (HCV) C-100 protein in a test sample which may contain the Hepatitis C Virus, comprising:

a. contacting the test sample with a first anti-HCV antibody or fragment thereof that specifically binds to HCV C-100 protein, said anti-HCV antibody or fragment attached to a solid phase, to form a mixture, wherein said first anti-HCV antibody is a monoclonal antibody secreted by a hybridoma selected from the group consisting of A.T.C.C. deposit Nos. 10593 and HB 10587;

b. incubating said mixture for a time and under conditions sufficient to form antigen/antibody complexes;

c. contacting said complexes with an indicator reagent comprising a signal generating compound which generates a measurable detectable signal attached to a second anti-HCV antibody secreted by a hybridoma selected from the group consisting of A.T.C.C. deposit Nos. 10593 and HB 10587, wherein said second antibody is not the same as said first antibody;

d. incubating said second mixture for a time and under conditions sufficient to form antibody/antigen/antibody complexes; and determining the presence of Hepatitis C Virus in the test sample by detecting the measurable signal generated, wherein the amount of HCV C-100 protein present in the test sample is proportional to said measurable generated signal.

9. A method for determining the presence of Hepatitis C Virus (HCV) 33C protein in a test sample which may contain the Hepatitis C Virus, comprising:

a. contacting the test sample with a first anti-HCV antibody or fragment thereof, wherein said antibody or fragment specifically binds to HCV 33C protein, said anti-HCV antibody or fragment attached to a solid phase, to form a mixture, wherein said first anti-HCV antibody is a monoclonal antibody secreted by a hybridoma selected from the group consisting of A.T.C.C. deposit Nos. 10594, HB 10589, HB 10607 and HB 10600;

b. incubating said mixture for a time and under conditions sufficient to form antigen/antibody complexes;

c. contacting said complexes with an indicator reagent comprising a signal generating compound which generates a measurable detectable signal attached to a second anti-HCV antibody which specifically binds to an HCV C-100 protein to form a second mixture, wherein said second anti-HCV antibody is a monoclonal antibody secreted by a hybridoma selected from the group consisting of A.T.C.C. deposit Nos. HB 10594, HB 10589, HB 10607 and HB 10600, and wherein said second antibody is not the same as said first antibody;

d. incubating said second mixture for a time and under conditions sufficient to form antibody/antigen/antibody complexes; and determining the presence of Hepatitis C Virus in the test sample by detecting the measurable signal generated, wherein the amount of HCV 33C protein present in the test sample is proportional to said measurable generated signal.

10. A method for determining the presence of Hepatitis C Virus (HCV) CORE protein in a test sample which may contain the Hepatitis C Virus, comprising:

a. contacting the test sample with a first anti-HCV antibody or fragment thereof, wherein said antibody or fragment specifically binds to HCV CORE protein, said anti-HCV antibody or fragment attached to a solid phase, to form a mixture, wherein said first anti-HCV antibody is a monoclonal antibody secreted by a hybridoma selected from the group consisting of A.T.C.C. deposit Nos. HB 10592, HB 10588, HB 10608, HB 10604 and HB 10602;

b. incubating said mixture for a time and under conditions sufficient to form antigen/antibody complexes;

c. contacting said complexes with an indicator reagent comprising a signal generating compound which generates a measurable detectable signal attached to a second anti-HCV antibody which specifically binds to an HCV CORE protein to form a second mixture, wherein said second anti-HCV antibody is a monoclonal antibody secreted by a hybridoma selected from the group consisting of A.T.C.C. deposit Nos. HB 10592, HB 10588, HB 10608, HB 10604 and HB 10602, and wherein said second antibody is not the same as said first antibody;

d. incubating said second mixture for a time and under conditions sufficient to form antibody/antigen/antibody complexes; and determining the presence of Hepatitis C Virus in the test sample by detecting the measurable signal generated, wherein the amount of HCV CORE protein present in the test sample is proportional to said measurable generated signal.

11. The method of anyone of claim 8, 9, or 10 wherein the signal generating compound is selected from the group consisting of a luminescent compound, a chemiluminescent compound, an enzyme and a radioactive element.

12. A competitive assay method for determining the presence and amount of Hepatitis C Virus (HCV) antibody which may be present in a test sample, comprising:

a. contacting a test sample suspected of containing HCV antibodies with a solid phase coated with HCV 33C, HCV C-100, or HCV CORE proteins and an indicator reagent comprising a signal generating compound which generates a measurable signal and a monoclonal antibody or fragment thereof, wherein said monoclonal antibody or fragment specifically binds to at least one of said HCV proteins, for a time and under conditions sufficient to form antigen/antibody complexes of test sample and solid phase and/or indicator reagent and solid phase, wherein when the solid phase is coated with HCV 33C protein, said monoclonal antibody is the monoclonal antibody secreted by hybridoma A.T.C.C. deposit No. HB 10594 or No. HB 10607; when the solid phase is coated with HCV C-100 protein, said monoclonal antibody is the monoclonal antibody secreted by hybridoma A.T.C.C. deposit No. HB 10593; and when the solid phase is coated with HCV CORE protein, said monoclonal antibody is the monoclonal antibody secreted by hybridoma A.T.C.C. deposit HB 10602; and b. determining the presence of HCV antibody present in the test sample by detecting the reduction in binding of the indicator reagent to the solid phase as compared to the signal generated from a negative test sample to indicate the presence of HCV antibody in the test sample.

13. The method of claim 12 wherein the signal generating compound is selected from the group consisting of a luminescent compound, a chemiluminescent compound, an enzyme and a radioactive element.

14. An assay kit for detecting the presence of Hepatitis C Virus (HCV) in a test sample comprising:

a container containing at least one monoclonal antibody or fragment thereof, wherein said at least one monoclonal antibody or fragment specifically binds to an HCV protein selected from the group consisting of HCV C-100 protein, HCV 33C protein and HCV CORE protein, wherein said at least one monoclonal antibody is a monoclonal antibody secreted by a hybridoma selected from the group consisting of A.T.C.C. deposit Nos. HB 10593, HB 10587, HB 10594, HB 10589, HB 10607, HB 10600, HB 10592, HB 10588, HB 10608, HB 10604 and HB 10602.

* * * * *

UNITED STATES PATENT AND TRADEMARK OFFICE
CERTIFICATE OF CORRECTION

PATENT NO. : 5,753,430
DATED : May 19, 1998
INVENTOR(S) : Mehta et al.

It is certified that error appears in the above-identified patent and that said Letters Patent is hereby corrected as shown below:

Column 8, line 44, change "0.2M" to --0.2 M--.

Column 10, line 32, change "supra" to --Supra--.

Column 15, line 37, change "157." to --157,--.

Column 16, line 64, change "72.313" to --72:313--.

Column 18, line 14, change "in" to --is--.

Signed and Sealed this

Twenty-seventh Day of April, 1999

Q. TODD DICKINSON

*Attest:*

*Attesting Officer*    *Acting Commissioner of Patents and Trademarks*